(12) United States Patent
Sankai

(10) Patent No.: US 11,654,035 B2
(45) Date of Patent: May 23, 2023

(54) GAIT DISORDER SUPPORT APPARATUS AND GAIT DISORDER SUPPORT METHOD

(71) Applicants: CYBERDYNE Inc., Tsukuba (JP); University of Tsukuba, Tsukuba (JP)

(72) Inventor: Yoshiyuki Sankai, Ibaraki (JP)

(73) Assignees: CYBERDYNE Inc., Tsukuba (JP); University of Tsukuba, Tsukuba (JP)

( * ) Notice: Subject to any disclaimer, the term of this patent is extended or adjusted under 35 U.S.C. 154(b) by 0 days.

(21) Appl. No.: 16/340,268

(22) PCT Filed: Mar. 17, 2017

(86) PCT No.: PCT/JP2017/011069
§ 371 (c)(1),
(2) Date: Apr. 8, 2019

(87) PCT Pub. No.: WO2018/066151
PCT Pub. Date: Apr. 12, 2018

(65) Prior Publication Data
US 2020/0039061 A1 Feb. 6, 2020

(30) Foreign Application Priority Data
Oct. 6, 2016 (JP) .............................. JP2016-198418

(51) Int. Cl.
*A61F 2/72* (2006.01)
*A61F 2/64* (2006.01)
*A61H 3/00* (2006.01)

(52) U.S. Cl.
CPC .................. *A61F 2/64* (2013.01); *A61F 2/72* (2013.01); *A61H 3/00* (2013.01); *A61H 2201/5061* (2013.01); *A61H 2201/5069* (2013.01)

(58) Field of Classification Search
CPC .. B25J 9/0006; A61H 3/00; A61H 2201/5061; A61H 2201/5069;
(Continued)

(56) References Cited

U.S. PATENT DOCUMENTS

| | | | | |
|---|---|---|---|---|
| 2005/0107889 | A1* | 5/2005 | Bedard | ..................... A61F 2/70 623/24 |
| 2009/0143870 | A1* | 6/2009 | Bedard | ..................... A61F 2/60 623/53 |

(Continued)

FOREIGN PATENT DOCUMENTS

| | | |
|---|---|---|
| EP | 2226006 A1 | 9/2010 |
| EP | 2671559 A1 | 12/2013 |

(Continued)

OTHER PUBLICATIONS

International Search Report and Written Opinion for related International Application No. PCT/JP2017/011069, dated Jun. 6, 2017; English translation of ISR provided; 8 pages.
(Continued)

*Primary Examiner* — Jerrah Edwards
*Assistant Examiner* — Aren Patel
(74) *Attorney, Agent, or Firm* — Procopio, Cory, Hargreaves & Savitch LLP

(57) ABSTRACT

A gait disorder support apparatus and gait disorder support method capable of detecting an onset sign of a gait disorder associated with motor symptoms in advance and performing motion assist are proposed. The onset sign of the gait disorder associated with the motor symptoms of a wearer is detected based on the correlation between a gait cycle and a reduction ratio of the gait cycle as compared to immediately preceding gait; and when the onset sign of the gait disorder is detected, a drive unit is controlled so that the drive unit applies assist power to a knee joint of the wearer; and on the (Continued)

other hand, when the onset sign of the gait disorder is not detected, the drive unit is controlled so that driving torque by the drive unit does not hinder the wearer's gait motion.

12 Claims, 16 Drawing Sheets

(58) Field of Classification Search
CPC ............ A61H 2201/5071; A61H 1/024; A61H 2205/12; A61H 2205/10; A61H 2201/0173; A61H 2203/007; A61H 2201/165; A61H 2201/5064; A61H 2201/5084; A61H 2230/085; A61H 2203/0406; A61H 2230/62; A61F 2/64; A61F 2/72
See application file for complete search history.

(56) References Cited

U.S. PATENT DOCUMENTS

| | | | | |
|---|---|---|---|---|
| 2010/0271051 | A1* | 10/2010 | Sankai | A61H 1/0262 324/679 |
| 2011/0288453 | A1 | 11/2011 | Endo | |
| 2013/0053736 | A1* | 2/2013 | Konishi | H01M 10/482 601/34 |
| 2014/0012164 | A1* | 1/2014 | Tanaka | A61F 2/72 601/35 |
| 2017/0043482 | A1* | 2/2017 | Hyun | B25J 9/0006 |
| 2017/0252255 | A1* | 9/2017 | Asano | B25J 9/163 |

FOREIGN PATENT DOCUMENTS

| | | |
|---|---|---|
| JP | 4390129 B2 | 12/2004 |
| JP | 2013-043055 A | 3/2013 |
| JP | 5251270 B2 | 7/2013 |
| JP | 2014-023795 A | 2/2014 |
| JP | 5588738 B2 | 9/2014 |
| JP | 2014195510 A | 10/2014 |
| JP | 2015-100529 A | 6/2015 |
| WO | 2013049658 A1 | 4/2013 |
| WO | 2014/208772 A1 | 12/2014 |
| WO | 2014194257 A1 | 12/2014 |
| WO | 2015088863 A2 | 6/2015 |
| WO | 2015164421 A1 | 10/2015 |

OTHER PUBLICATIONS

Extended European Search Report for related EP App No. 17857991.8 dated Apr. 23, 2020, 9 pgs.

Response to Search Report for related EP App No. 17857991.8 dated Nov. 20, 2020, 18 pgs.

* cited by examiner

Stance phase · Swing phase

FIG.18
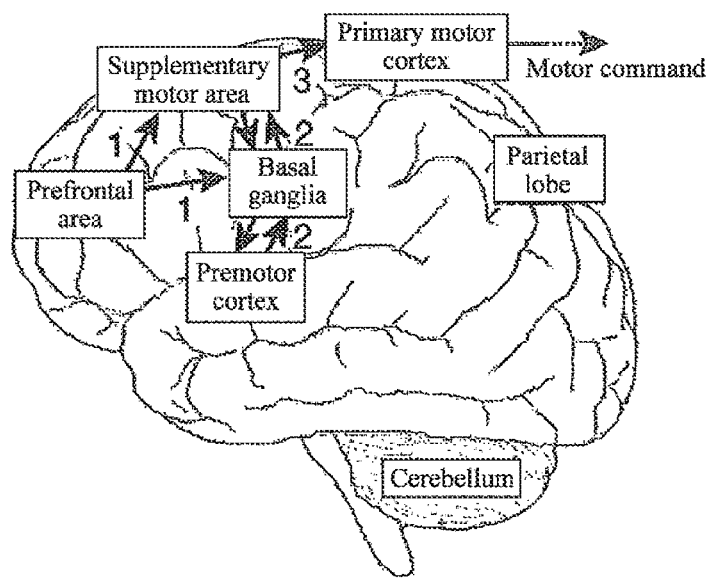
(A) Normal gait
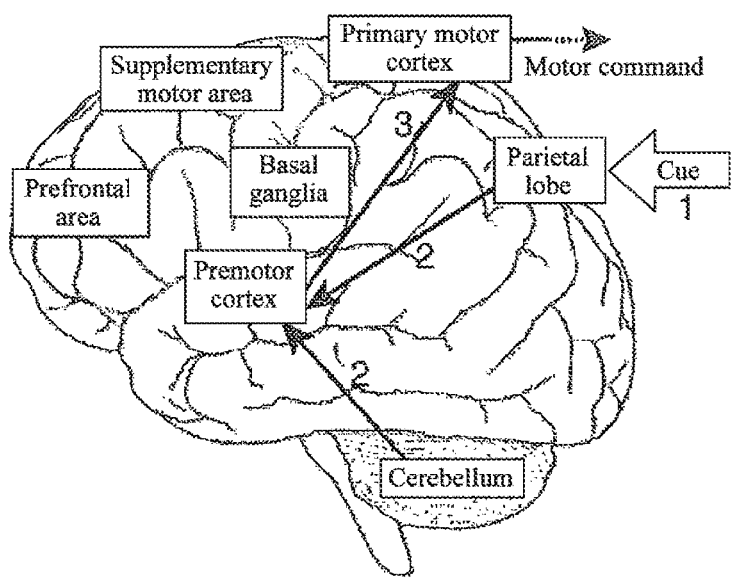
(B) Gait with external cue at freeze

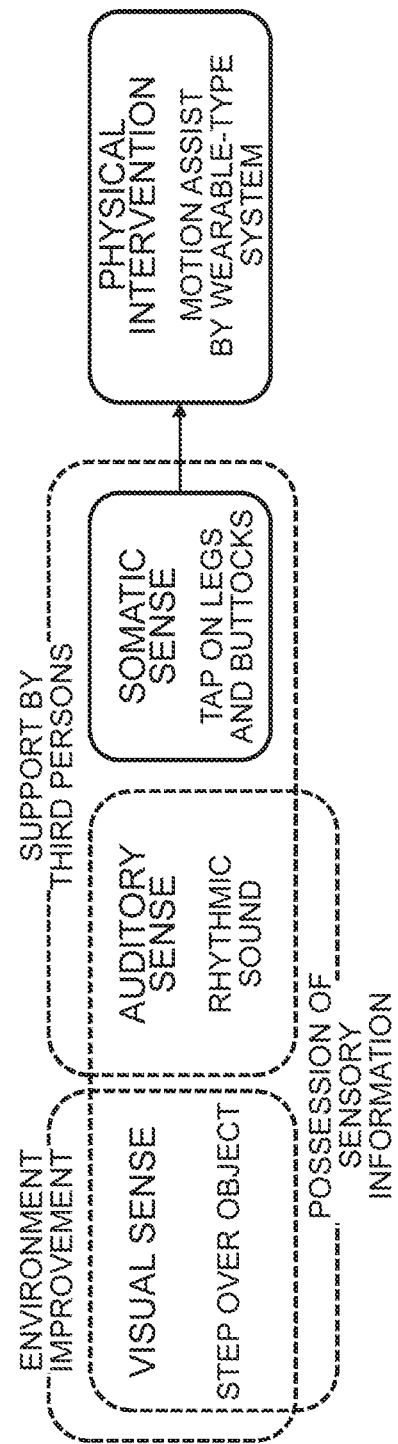

GAIT DISORDER SUPPORT APPARATUS AND GAIT DISORDER SUPPORT METHOD

CROSS-REFERENCE TO RELATED APPLICATIONS

This application is a U.S. National Stage entry of PCT Application No: PCT/JP2017/011069 filed Mar. 17, 2017, which claims priority to Japanese Patent Application No. 2016-198418, filed Oct. 6, 2016, the contents of which are incorporated herein by reference.

TECHNICAL FIELD

The present invention relates to a gait disorder support apparatus and a gait disorder support method and is suited for use in a wearable-type motion assist apparatus for detecting onset signs of a gait disorder associated with motor symptoms.

BACKGROUND ART

Parkinsonism is a motor disorder which causes difficulties in standing up or walking with the progression of its symptoms, and is caused by, for example, Parkinson's disease (PD) and other degenerative diseases, cerebrovascular disorders, and drug administration. The parkinsonism indicates a condition where two or more of the following apply: a tremor generating periodic shivering of approximately 6 Hz which is a characteristic symptom of the Parkinson's disease; muscle rigidity which generates cogwheel resistance when bending and extending joints; akinesia which causes sluggish motions; and a postural reflex disorder which causes difficulties in maintaining the posture due to insufficient reflexive muscle contraction. The parkinsonism is classified into symptomatic parkinsonism and essential parkinsonism depending on whether a disease or an inducer which causes the onset of the disease state is clear or not.

Particularly, the parkinsonism which is caused by cerebrovascular disorders such as a multiple cerebral infarction is called "vascular parkinsonism (VP)" and it is assumed that the number of affected patients of the vascular parkinsonism will continue to increase as a result of an increase of cerebrovascular disorder patients in association with aging of the population.

Regarding the multiple cerebral infarction, many blood vessels that nourishes the brain are blocked by a lacunar infarction which is a minute infarction of the diameter of 15 mm or less, so that sufficient oxygens and nourishment are not supplied to cell tissues, thereby causing localized necrosis.

Regarding dynamics of various nuclei related to motion control of the multiple cerebral infarction presenting with the parkinsonism, firstly nerve cells which accept dopamine of putamen degenerate and decrease due to the lacunar infarction. Next, the reduction in a received amount of the dopamine causes excessive suppression of the globus pallidus external segment by the putamen; and as suppression of the subthalamic nucleus decreases, the subthalamic nucleus is caused to become hyperactive. Subsequently, the subthalamic nucleus implements excessive canalization on the globus pallidus internal segment and the globus pallidus internal segment excessively suppresses the thalamus. As a result of the reduction of the canalization from the thalamus, output from the cerebral cortex to the spinal cord reduces, thereby suppressing motility.

Consequently, the vascular parkinsonism causes the nerve cells, which accept the dopamine, that is, a neurotransmitter, to degenerate in the basal ganglia which has a motor coordination function such as controlling contractions of skeletal muscles in an unconscious state during gait, so that motor disorders appear. On the other hand, regarding the Parkinson's disease, the nerve cells which produce the dopamine of the midbrain substantia nigra compacta degenerate for whatever reason and a release amount of the dopamine decreases.

Accordingly, although the mechanism of reduction of the received amount of the dopamine differs between the Parkinson's disease and the vascular parkinsonism, the basal ganglia is affected by deficiency in the dopamine in both cases and, therefore, there is similarity in the expressed disease state between them. So-called "frozen gait" among the motor disorders is a gait disorder which appears in approximately 50% of the Parkinson's disease patients and shows symptoms such as inability to move legs as if feet were stuck to the floor when walking.

The frozen gait is the main cause of falls and may result in chronic bruise marks by hitting their face hard or frequently falling on their knees. Also, the occurrence of the frozen gait is unpredictable, and a patient cannot control the symptom by themselves upon the occurrence and cannot walk until the frozen gait is resolved.

Accordingly, the gait disorder causes not only degradation of ADL (Activities of Daily Living), but also mental influences such as confusion arisen by the occurrence of the frozen gait and fear and anxiety of falls, thereby bringing about significant degradation of QOL (Quality of Life). Therefore, it is very important to solve the problems of the frozen gait.

Conventional physical therapies for the Parkinson's disease patients who suffer from the frozen gait use external cues with the purpose of providing cues to promote resumption of walking such as stepping over a pattern on, or a tape pasted on, the floor face, presenting rhythmic sound information using a metronome or a third person's call, and lightly tapping on the buttocks or legs.

FIG. 18A illustrates the outline of activities of a healthy person's cranial nervous system during normal gait; and FIG. 18B illustrates the outline of activities of the Parkinson's disease patient's cranial nervous system during gait using the external cue. When the healthy person walks, firstly the prefrontal area which serves thinking, creativity, recognition, and execution functions makes decisions. Then, signals are transmitted to the supplementary motor area which serves to start and control voluntary movements, the basal ganglia which serve to adjust movements, and the premotor area which serves to control movements based on sensory information. Eventually, inputs are bound together in the primary motor area, thereby generating a motor command.

When the Parkinson's disease patient walks by using the external cues, signals are transmitted from the parietal lobe, which serves to perceive stimuli inside and outside the body, and the cerebellum, which performs feedforward control of the movements, to the premotor area. Subsequently, a motor command is generated in the primary motor area.

Consequently, the external cues realize instantaneous improvements of the gait disorder by using a compensatory nervous system without via, for example, the supplementary motor area and/or the basal ganglia which have been damaged, so that the external cues have been widely used for the physical therapies.

FIG. 19 illustrates the external cues for the frozen gait. Support by the external cues requires improvements of the environment and human assistance, but it is difficult to constantly improve the environment and provide the support by a third person(s) with respect to the frozen gait which happens in daily life. Accordingly, the support by a wearable-type system is appropriate. Furthermore, in order to provide the gait support for the frozen gait which occurs in the daily life, an intervention method which does not occupy the visual sense or the auditory sense and is not influenced by the external environment is required as an assistance method.

Consequently, it is considered appropriate to use a method of providing the motion assist which does not act on the visual sense or the auditory sense, but enables legs to take steps forward by means of the motion assistance from outside.

For example, there is proposed a gait motion assistance apparatus designed to be capable of assisting legs to take steps forward by detecting a transition from a first state of a subject's leg in motion to a second state where that leg stagnates (the frozen gait), and enhancing output of an actuator for assisting the leg's motion in a stepwise manner (see PTL 1).

Firstly, as a method for detecting the frozen gait, there is also proposed a lower limb joint moment estimation system that makes it possible to judge effectiveness of rehabilitation by estimating a moment and muscle tonus of each joint during gait by using positional (locus) information of the subject's each joint (ankle joints, knee joints, and hip joints) and an estimated value of floor reaction force on the foot soles (see PTL 2).

Secondly, there is also proposed an evaluation apparatus for treating time series data of rhythms for repetitive rhythmic movements by the subject's voluntary movements as biological signal information and evaluating the condition of the Parkinson's disease based on the relevant rhythm cycle or an increase/decrease of its average value (see PTL 3).

CITATION LIST

Patent Literature

PTL 1: Japanese Patent No. 5588738
PTL 2: Japanese Patent No. 4390129
PTL 3: Japanese Patent No. 5251270

SUMMARY OF THE INVENTION

Problems to be Solved by the Invention

However, since the gait motion assistance apparatus according to PTL 1 processes and analyzes the signals after the onset of the frozen gait, there is a lag in response. Also, after the onset of the frozen gait, muscle activities to bend and extend lower leg muscle groups become hyperactive. Accordingly, it is desirable that the gait support for the frozen gait in the actual environment should provide the motion assist by detecting the onset of the frozen gait in advance.

Furthermore, although the detection and evaluation methods of PTL 2 and PTL 3 can detect a sign for the frozen gait by detecting the subject's gait condition, neither PTL 2 nor PTL 3 refer to the relation with the gait support by the actual motion assist apparatus and there are problems of insufficiency for practical use with respect to, for example, prompt provision of the motion assist and whether or not the motion assist is performed when the frozen gait is not detected.

The present invention was devised in consideration of the above-described circumstances and aims at proposing a gait disorder support apparatus and gait disorder support method capable of detecting an onset sign of the gait disorder associated with motor symptoms in advance and performing the motion assist.

Means to Solve the Problems

In order to solve the above-described problems, the present invention includes: a drive unit that drives frames mounted on a thigh part and a lower leg part of either a right leg or a left leg of a wearer relatively around a rotation axis corresponding to a knee joint of the wearer; a foot load measurement unit that is attached to right and left foot sole surfaces of the wearer and measures a load imposed on a front foot part of each of the foot sole surfaces; a gait cycle calculation unit that calculates, as a gait cycle, an occurrence timing regarding the leg on which the drive unit is mounted among occurrence timings of a peak value of the load measured by the foot load measurement unit; an onset sign detection unit that detects an onset sign of a gait disorder associated with a motor symptom of the wearer on the basis of a correlation between the gait cycle calculated by the gait cycle calculation unit and a reduction ratio of the gait cycle as compared to immediately preceding gait; and a control unit that controls the drive unit so that the drive unit applies assist power to the knee joint of the wearer when the onset sign of the gait disorder is detected by the onset sign detection unit, while controlling the drive unit so that driving torque by the drive unit does not interfere with a gait motion of the wearer when the onset sign of the gait disorder is not detected.

As a result, the gait disorder support apparatus can detect the onset sign of the gait disorder associated with the motor symptom of the wearer in advance, the gait motion will not be hindered by the drive unit during the normal gait, and the motion assist can be provided by means of the drive unit when the onset sign of the gait disorder is detected, so that optimum gait support for the gait disorder can be realized in the actual environment.

Furthermore, according to the present invention, when the gait cycle by the gait cycle calculation unit fails to satisfy a predetermined threshold value continuously for a specified number of times or more, the onset sign detection unit detects this gait cycle as the onset sign of the gait disorder associated with the motor symptom of the wearer. As a result, the gait disorder support apparatus can complementarily detect the onset sign of the gait disorder associated with the wearer's motor symptom.

Furthermore, according to the present invention, the foot load measurement unit measures the load imposed not only on the front foot part of the right and left foot sole surfaces of the wearer, but also on a middle foot part and a rear foot part; and wherein while detecting a gravity center position during the wearer's gait motion based on a change in the load measured by the foot load measurement unit, the control unit controls the drive unit so that the drive unit applies the assist power in synchronization with timing when the gravity center position is located at the wearer's leg on which the drive unit is not mounted.

As a result, when the onset sign of the gait order associated with the wearer's motor symptom is detected, the assist power by the drive unit can be applied at the timing when the wearer's own weight is not imposed on the leg on which the drive unit is not mounted; and the safety can be secured by avoiding the fear of falls as a result of applying the assist power at the timing when the wearer's own weight is imposed on the leg on which the drive unit is mounted.

Furthermore, according to the present invention, when the onset sign is detected by the onset sign detection unit, the control unit adjusts size and duration of the assist power generated by the drive unit in accordance with a gait motion condition of the wearer.

As a result, when the wearer's motor symptom is relatively severe, the motion assist can be applied to bend the knee joint to a target angle (for example, the maximum bending position during gait); and on the other hand, when the motor symptom is relatively light, the motion assist can be applied to a degree of lightly bending the knee joint for a moment.

Furthermore, according to the present invention, the control unit executes specified smoothing processing for a specified amount of time after generation of the driving torque is started by the drive unit. As a result, at the moment when the driving torque by the drive unit is applied to the wearer and the joint assist motion is started, the occurrence of physical burdens can be avoided by preventing induction of antagonist muscles against the support torque.

Furthermore, according to the present invention, during a period of time when the onset sign is not detected by the onset sign detection unit, the control unit causes a sum of viscous friction compensating torque applied to the drive unit and gravity compensating torque applied to the frames to act as the driving torque by the drive unit in order to not hinder the gait motion of the wearer.

As a result, during the wearer's gait motion, the wearer can perform the gait motion in a natural state without any influence of the driving torque by the drive unit.

Furthermore, according to the present invention, a drive unit is designed to drive frames mounted on a thigh part and a lower leg part of either a right leg or a left leg of a wearer relatively around a rotation axis corresponding to a knee joint of the wearer, such that gait disorder support apparatus does not assist an other of a left leg or a right leg of the wearer, and the present invention includes: first processing for measuring a load imposed on a front foot part of each of right and left foot sole surfaces of the wearer and calculating, as a gait cycle, an occurrence timing regarding the leg on which the drive unit is mounted among occurrence timings of a peak value of the measured load; second processing for detecting an onset sign of a gait disorder associated with a motor symptom of the wearer on the basis of a correlation between the gait cycle and a reduction ratio of the gait cycle as compared to immediately preceding gait; and third processing for controlling the drive unit for the drive unit to apply assist power to the knee joint of the wearer when the onset sign of the gait disorder is detected, while controlling the drive unit so that driving torque by the drive unit does not interfere with a gait motion of the wearer when the onset sign of the gait disorder is not detected.

As a result, according to the gait disorder support method, the onset sign of the gait disorder associated with the wearer's motor symptom can be detected in advance, the gait motion will not be hindered by the drive unit during the normal gait, and the motion assist can be provided by the drive unit when the onset sign of the gait disorder is detected, so that the optimum gait support for the gait disorder can be realized in the actual environment.

Advantageous Effects of the Invention

The gait disorder support apparatus and gait disorder support method capable of resolving the symptoms of the frozen gait and enabling the wearer to resume walking by means of physical intervention which does not occupy the visual sense or the auditory sense and is not influenced by the external environment can be realized according to the present invention.

BRIEF DESCRIPTION OF DRAWINGS

FIG. 18 is a diagram illustrating the outline of activities of a conventional cranial nervous system; and FIG. 19 is a conceptual diagram illustrating a solution method (external cue) when conventional frozen gait happens.

DESCRIPTION OF EMBODIMENTS

An embodiment of the present invention will be explained below in detail with reference to the drawings.

(1) Gait Disorder Support for Frozen Gait According to the Present Invention

So-called "frozen gait" is defined as a lack or a significant reduction of forward advance of lower limbs, which may sometimes happen in a short time, regardless of the intention to walk. Examples of the relevant symptoms include the incapability to move the feet away from the ground and the occurrence of slight shaking in the lower limbs; and the frozen gait tends to easily occur in the circumstances such as when starting walking or turning in direction, in front of a movement target such as a chair or a bed, and when passing through a narrow space.

Furthermore, the gait ability changes diurnally, which is the characteristic that can rarely be observed with other diseases. So, although the symptoms cannot be often seen in rehabilitation scenes, the Parkinson's disease patients sometimes complain about their difficulty, which can be hardly imagined from the rehabilitation scenes, in walking in patient rooms or in daily life.

Hoehm-Yahr Classification of Disability scale is used as an index for indicating the degree of symptoms of the Parkinson's disease when designing a treatment plan. This classifies severity classification levels into five stages: a first stage is symptoms on one side and mild disorder; a second stage is mild disorder on both sides; a third stage is a moderate degree of disorder on both sides; a fourth stage is a state where it is difficult to lead a self-sustaining daily life; and a fifth stage is a state of being on a wheelchair or bedridden.

Since the present invention is aimed at the gait support for the frozen gait, a patient who suffers from the frozen gait and disorder of the severity classification levels from the first stage to the fourth stage with the ability to walk by themselves is assumed to be a wearer.

According to the present invention, a motion assist apparatus is mounted on at least one leg of the wearer and the optimum gait support for the frozen gait can be realized in the actual environment by performing the motion assist while detecting an onset sign of the gait disorder associated with the wearer's motor symptom in advance.

Figure 1:
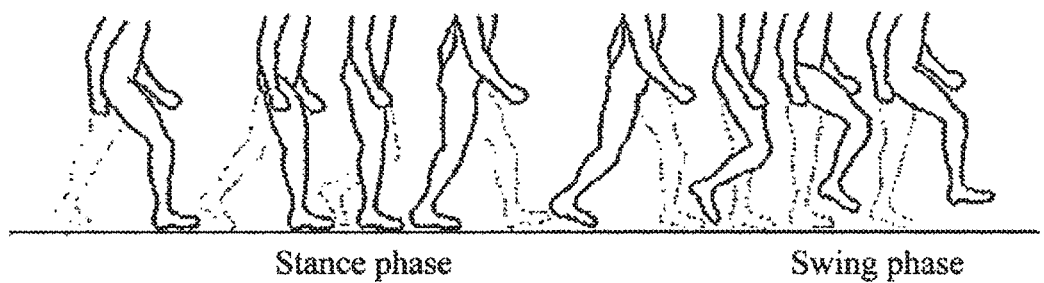
FIG. 1 is a conceptual diagram illustrating walking and a gait cycle.

Walking is motions to move the body by repeating motions by two lower limbs as illustrated in FIG. 1. Since analysis of walking can be expressed comprehensively based on the cyclic nature, a gait cycle (GC) is used in many cases. The gait cycle is mainly classified into a stance phase during which a foot part which is being observed is touching the ground, and a swing phase during which a lower limb stays in the air and advances in order to functionally divide lower limb activities.

Furthermore, the stance phase and the swing phase are subdivided into a total of eight periods in terms of impact absorption, weight support, and advancing. During a stance end phase which is one of divisions of the stance phase, the body weight is imposed only on the front foot part in a single leg state during gait, so that toe floor reaction force (tFRF) is expressed as in FIG. 2.

According to the present invention, the gait cycle is calculated by defining the toe floor reaction force (tFRF) at its peak as a start point of the gait cycle. Also, it is confirmed that upon the onset of the frozen gait, the foot soles cannot be completely moved away from the ground and the gait cycle reduces immediately before the onset by 35.2% of the gait cycle during normal gait.

Under this circumstance, when a gait cycle reduction ratio (GCRR) as compared to the immediately preceding gait is defined as $GCRR_n$ where $GC_n$ represents the gait cycle (that is, a peak interval of tFRF) at an n-th step, $GCRR_n$ is expressed as the following Expression (1).

[Math. 1]

$$GCRR_n = \begin{cases} 1 & (n=1) \\ \dfrac{GC_n}{GC_{n-1}} & (n>1) \end{cases} \quad (1)$$

According to this Expression (1), the present invention detects a "behavior" which is expressed immediately before the onset of the frozen gait by calculating and comparing $GC_n$ and $GCRR_n$ for each gait on a real-time basis.

The disease state of the parkinsonism is influenced by various elements such as disease duration, external factors such as air temperature and humidity, side effects of drugs being taken, and diurnal variations due to wearing-off, so that reproducibility of the frozen gait is poor and it is difficult to take initiative to set parameters for the detection.

So, according to the present invention, parameters regarding detection of the onset of the frozen gait can be adjusted semi-automatically without requiring any special experience by using cluster analysis on data group on a GC-GCRR plane.

Firstly, according to the present invention, the gait cycle GC and the reduction ratio GCRR during the normal gait and upon the onset of the frozen gait of a user are measured and the cluster analysis of the measured samples is performed. This cluster analysis implements classification into a cluster $C_{Walking}$ during the normal gait and a cluster $C_{FOG}$ upon the onset of the frozen gait and calculation of a centroid which is the center of gravity of each cluster. Regarding samples obtained for each gait after the cluster analysis, a norm between each sample and each centroid is calculated. It is judged that this sample belongs to the cluster regarding which the calculated norm is small.

Accordingly, when regarding the GC-GCRR plane, a coordinate vector of an input sample of the n-th step is defined as $x_n$, centroid coordinate vectors of $C_{Walking}$ and $C_{FOG}$ are defined as $C_{Walking}$ and $C_{FOG}$ respectively, norms between the respective centroids and the input samples are defined as $L_{Walking}$ and $L_{FOG}$ respectively, and a constant for adjusting detection sensitivity of the frozen gait is defined as α, $L_{Walking}$, $L_{FOG}$, and a frozen gait onset detection condition are expressed as the following Expressions (2) to (4), respectively.

[Math. 2]

$$L_{Walking} = \|c_{Walking} - x_n\| \quad (2)$$

[Math. 3]

$$L_{FOG} = \|c_{FOG} - x_n\| \quad (3)$$

[Math. 4]

$$\alpha L_{FOG} < L_{Walking} \quad (0 < \alpha \le 1) \quad (4)$$

Under this circumstance, the gait state needs to be separated into two $C_{Walking}$ and $C_{FOG}$ regarding the detection of the onset of the frozen gait during gait, so that hierarchical clustering by setting the number of clusters as two is employed. The norms between each sample and the clusters are Euclidean distances and the method of elastic center is used as a combining method.

Figure 3:
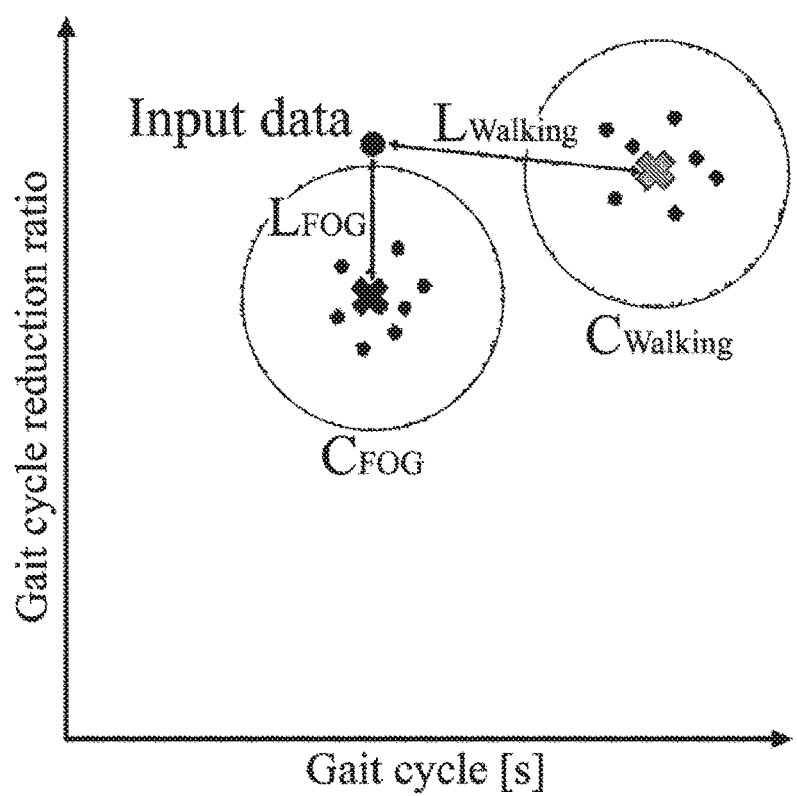
FIG. 3 is a chart representing the correlation between the gait cycle and its reduction ratio.

During the normal gait, $GC_n$ is almost constant and $GCRR_n$ thereby becomes approximately 1; and immediately before the onset of the frozen gait, $GCRR_n$ becomes smaller along with a reduction of $GC_n$. Therefore, the respective samples are in the positional relationship as illustrated in FIG. 3 when the vertical axis represents GCRR and the horizontal axis represents GC.

Figure 4:
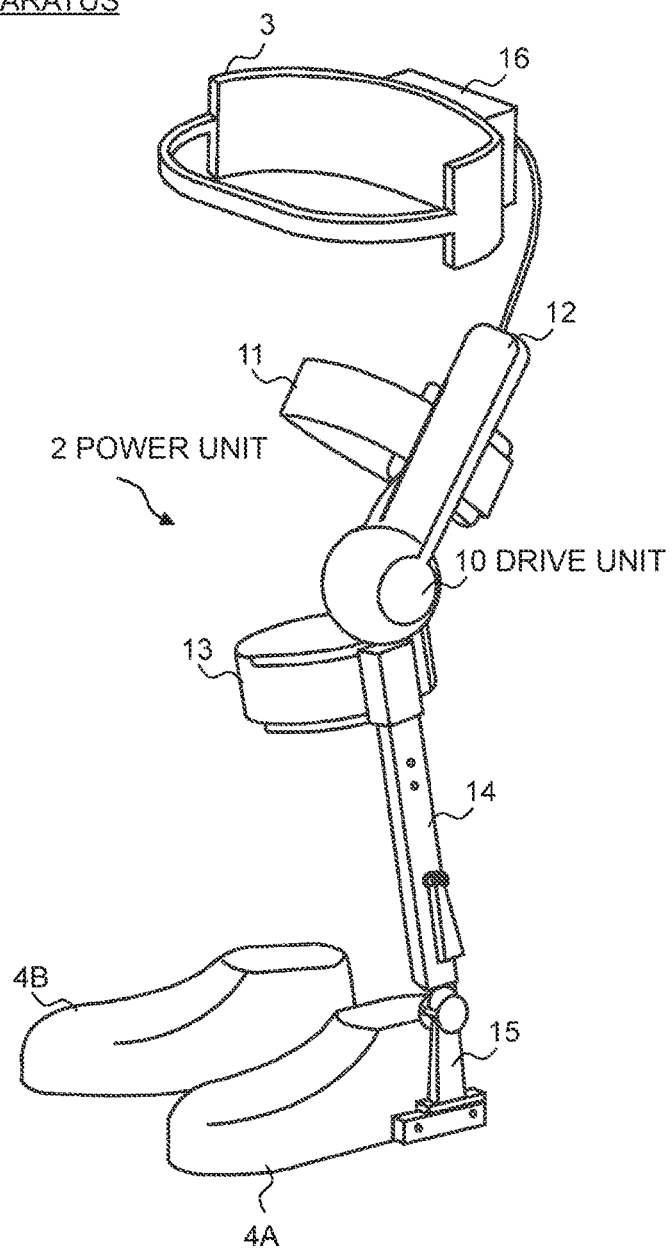
FIG. 4 is an external view illustrating an overall configuration of a gait disorder support apparatus according to an embodiment of the present invention.

(2) Configuration of Gait Disorder Support Apparatus According to this Embodiment FIG. 4 illustrates an exoskeleton-type gait disorder support apparatus 1 for a single leg according to this embodiment. The gait disorder support apparatus 1 includes: a power unit 2 to be attached to around a knee joint of a wearer's left leg; a lower back belt 3 to be attached to the wearer's lower back; and a pair of dedicated shoes 4A, 4B to be worn by the wearer's both feet.

The power unit 2 includes: a drive unit 10 including an actuator located on a lateral side of the wearer's left knee joint; a first transmission member (frame) 12 fastened to a thigh part of the wearer's left leg via a fastening member 11; and a second transmission member (frame) 14 fastened to the wearer's left shin via a fastening member 13. Therefore, the power unit 2 can relatively drive the first and the second transmission members 12, 14 around an output shaft of the actuator corresponding to the wearer's left knee joint.

Furthermore, the first transmission member 12: is equipped with a control device 20 (FIG. 5) which performs integrated control of the entire apparatus; and is also equipped with a sensor group (not illustrated in the drawing) for detecting driving torque, a rotation angle, etc. of the actuator.

Incidentally, each of the first and second transmission members 12, 14 has a frame body formed in a long plate shape made of, for example, metal such as stainless steel or carbon fibers and is formed to be lightweight and have high rigidity. In this embodiment, carbon fiber reinforced plastic (CFRP) and extra-super duralumin, which is an aluminum alloy, are used as strength members.

Furthermore, each of the fastening members 11, 13 is formed of, for example, a cloth-made belt and is designed to be firmly retained at the wearer's left leg via an insertion part which is inserted into the relevant first or second transmission member 12, 14.

A held part 15 which is secured to, and held at, a lateral-side coupling part of the dedicated shoes 4A, 4B for the left foot to be worn by the wearer is coupled to the second transmission member 14 in a freely movable manner at a lower end of the frame body. These dedicated shoes 4A, 4B have the configuration of a pair of right and left parts, are to hold the wear's feet from the tips of their toes to their ankles in a closely fitted manner, and are capable of measuring load with floor reaction force sensors (FRF sensors 50 described later) provided at their soles.

Incidentally, the lower back belt 3 to be attached to the wearer's lower back is equipped with a battery unit 16 for supplying a drive power source for the entire apparatus.

(3) Internal System Configuration of Gait Disorder Support Apparatus

Figure 5:
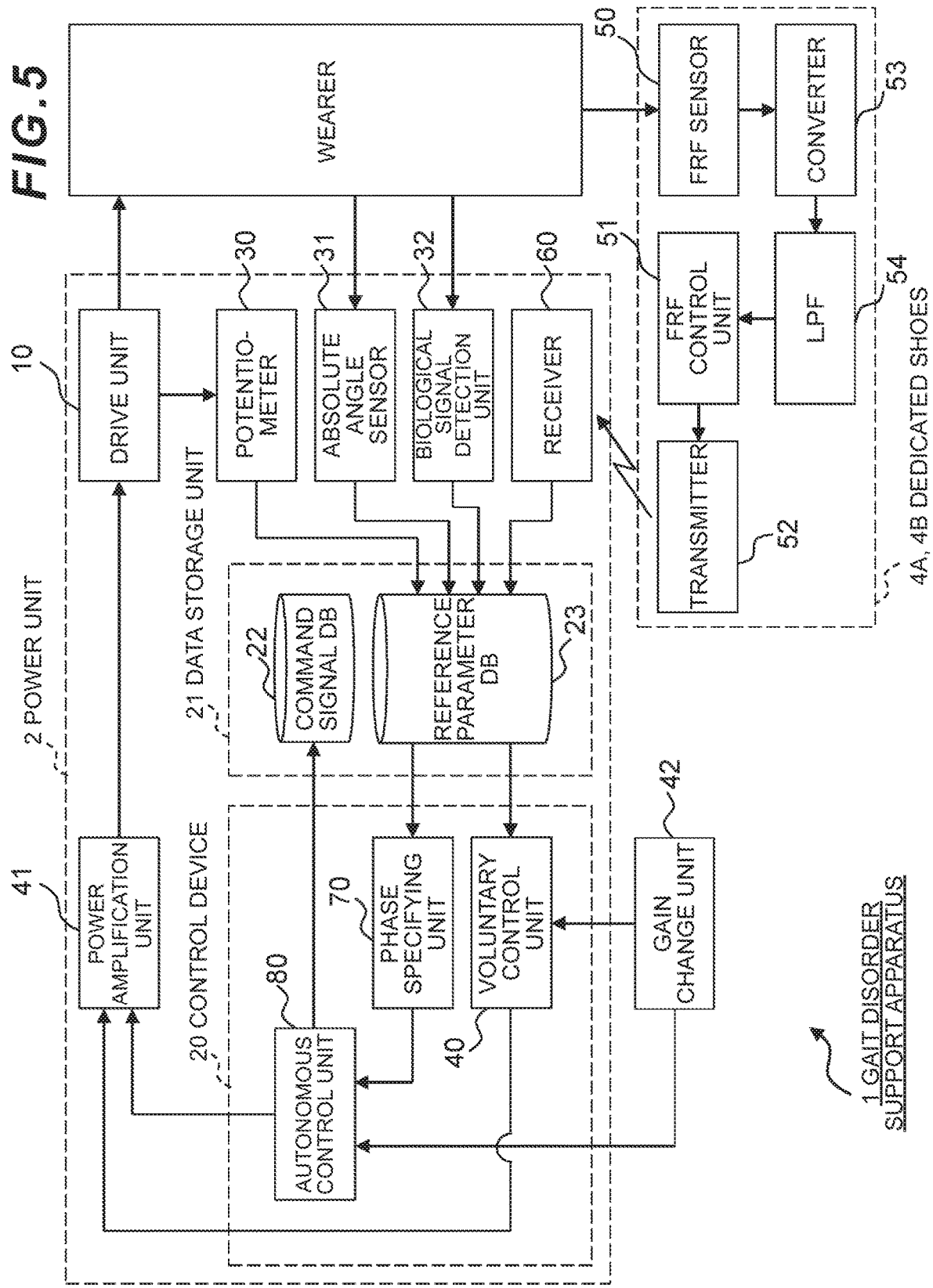
FIG. 5 is a block diagram illustrating the configuration of a control system of the gait disorder support apparatus according to the embodiment of the present invention.

FIG. 5 illustrates the configuration of a control system for the gait disorder support apparatus 1 according to this embodiment. The control system is mainly built in the power unit 2. The control system includes: the control device 20 which performs integrated control of the entire apparatus; a data storage unit 21 in which various kinds of data are formed into databases in a writable and readable manner in accordance with commands from the control device 20; and the drive unit 10 composed of the actuator which applies the assist force to the wearer.

Furthermore, a potentiometer 30 for detecting a rotation angle of an output shaft of the actuator for the drive unit 10 is provided coaxially with the output shaft so as to detect a knee joint angle according to the wearer's motions. Furthermore, the first transmission member 12 for the power unit 2 is equipped with an absolute angle sensor 31 for measuring an absolute angle relative to a vertical direction of the thigh part.

This absolute angle sensor 31 is composed of an acceleration sensor and a gyrosensor and is used for sensor fusion which is a method for extracting new information by using a plurality of pieces of sensor data. For the calculation of the absolute angle of the thigh part, a primary filter is used to eliminate influences of translational motion and temperature drift at each sensor. This primary filter is calculated by applying weighting and adding weight to a value obtained from each sensor. When the absolute angle relative to the vertical direction of the thigh part is defined as $\theta_{abs}(k)$, angular velocity obtained by the gyrosensor is defined as $\omega$, a sampling period is defined as dt, and acceleration obtained by the acceleration sensor is defined as $\alpha$, $\theta_{abs}(t)$ is expressed as the following Expression (5).

[Math. 5]

$$\theta_{abs}(k)=0.95*(\theta_{abs}(k-1)++0.05*\alpha \tag{5}$$

Furthermore, a biological signal detection unit 32 composed of a biological signal detection sensor is located on a body surface of the wearer's left thigh part and is designed detect a bioelectric potential signal to move the wearer's left knee joint.

The data storage unit 21 stores a command signal database 22 and a reference parameter database 23.

A voluntary control unit 40 supplies a command signal according to the detection signal of the biological signal detection unit 32 to a power amplification unit 41.

The voluntary control unit 40 generates a command signal by applying a specified command function f(t) or gain P to the biological signal detection unit 32. This gain P is a preset value or function and can be adjusted via a gain change unit 42 by external input.

Furthermore, it is also possible to select a method for controlling the driving torque (torque size and rotation angle) of the actuator based on angle data of the knee joint which is detected by the potentiometer 30. This method is effective, for example, in the case where the degree of the gait order associated with the wearer's motor symptom is relatively light and the case where it is anticipated that the wearer's skin will become wet with sweat and there is a possibility that the input of the biological signal from the biological signal detection unit 32 could not be obtained.

Data of the knee joint angle detected by the potentiometer 30, data of the absolute angle relative to the vertical direction of the thigh part which is detected by the absolute angle sensor 31, and the biological signal detected by the biological signal detection unit 32 are input to the reference parameter database 23.

Furthermore, the FRF (floor reaction force) sensors 50 are provided at the soles of the one pair of dedicated shoes 4A, 4B and detect a reaction force to the load imposed on the wearer's right and left foot sole surfaces. This FRF sensor 50 can measure the load imposed on the foot sole surface by dividing the load into a front foot part (toe part) and a rear foot part (heel part) and measuring the divided loads independently.

This FRF sensor 50: is composed of, for example, a piezoelectric device for outputting a voltage according to the applied load and a sensor with an electrostatic capacity which changes according to the load; and can detect changes in the load in association with movements of the body weight and whether the wearer's legs are in contact with the ground or not.

Figure 6:
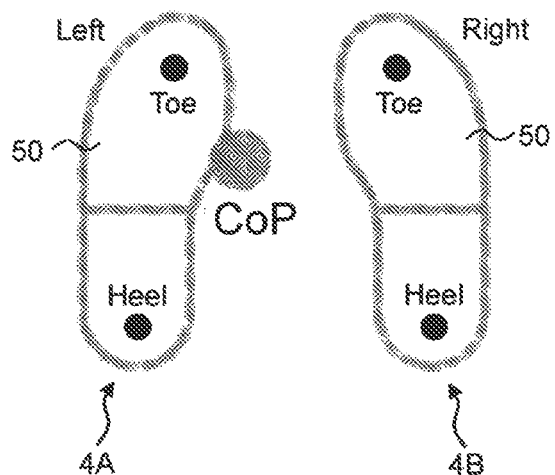
FIG. 6 is a conceptual diagram for explaining how to find a gravity center position from load balance relating to right and left foot sole surfaces.

Furthermore, regarding the one pair of dedicated shoes 4A, the gravity center position CoP can be found based on balance of the load relating to the right and left foot sole surfaces based on the detection results of the respective FRF sensors 50 as illustrated in FIG. 6. Accordingly, with the one pair of dedicated shoes 4A, 4B, it is possible to estimate on which side of the wearer's right and left legs the center of gravity is biased, based on the data measured by the respective FRF sensors 50.

Each dedicated shoe 4A, 4B includes, other than the shoe configuration, an FRF control unit 51, which is composed of the FRF sensor 50 and an MCU (Micro Control Unit), and a transmitter 52. After the output from the FRF sensor 50 is converted into a voltage via a converter 53, a high frequency band is blocked via an LPF (Low Pass Filter) 54 and the obtained voltage is input to the FRF control unit 51.

This FRF control unit 51 finds: changes in the load in association with movements of the wearer's body weight and whether the relevant foot is in contact with the ground or not, based on the detection results of the FRF sensor 50; and also finds the gravity center position according to the load balance relating to the right and left foot soles. The FRF control unit 51 wirelessly transmits the found gravity center position as FRF data via the transmitter to a receiver 60 in the power unit 2.

After receiving the FRF data wirelessly transmitted from the transmitter 52 of each dedicated shoe 4A, 4B via the receiver 60, the power unit 2 stores the load and the gravity center position relating to the right and left foot soles based on the FRF data in the reference parameter database 23 of the data storage unit.

The phase specifying unit 70 compares the data of the knee joint angle detected by the potentiometer 30 and the data of the load detected by the FRF sensor 50 with the knee joint angle and the load which are reference parameters stored in the reference parameter database 23. The phase specifying unit 70 specifies the wearer's motion phase based on this comparison result.

Then, after obtaining control data of the phase specified by the phase specifying unit 70, the autonomous control unit 80 generates a command signal according to the control data of this phase and supplies the command signal, which is for the drive unit 10 to generates this motive power, to the power amplification unit 41.

Furthermore, the gain adjusted by the aforementioned gain change unit 42 has been input to the autonomous control unit 80, which generates a command signal according to this gain and outputs the command signal to the power amplification unit 41. The power amplification unit 41 controls the torque size and rotation angle of the actuator by controlling an electric current for driving the actuator of the drive unit 10 and thereby applies the assist force by the actuator to the wearer's left knee joint.

Accordingly, the gait disorder support apparatus 1 executes various processing based on the detection signal detected by the biological signal detection sensor of the biological signal detection unit 32 pasted on the wearer's left thigh part. Specifically speaking, the control signal for controlling the actuator of the drive unit 10 is amplified by the power amplification unit 41 and supplied to the actuator of the drive unit 10. Also, the torque of this actuator is transmitted as the assist force to the wearer's left knee joint via the first and second transmission members 12, 14.

(4) Drive Unit Control Method During Normal Gait

Figure 2:
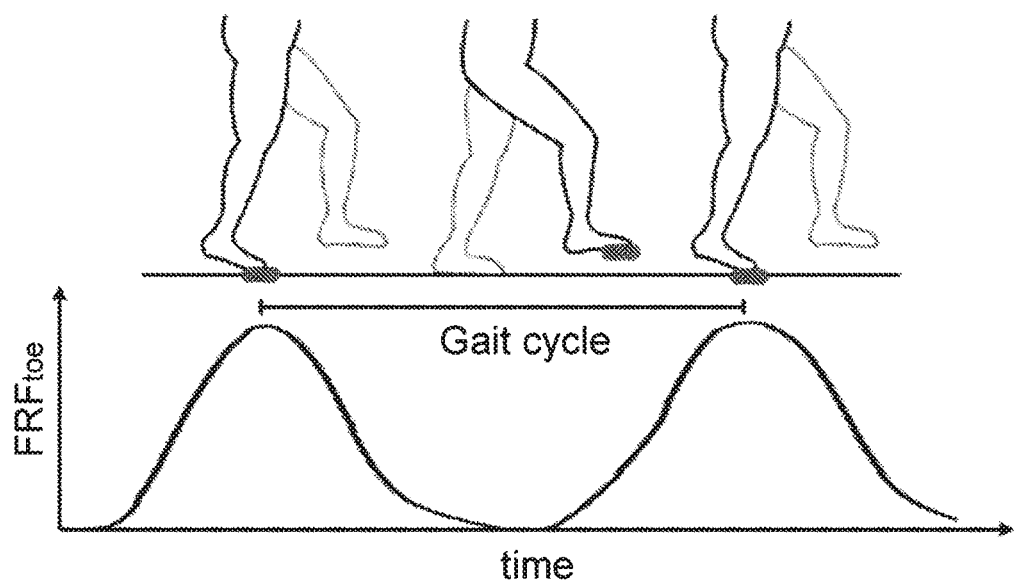
FIG. 2 is a conceptual diagram for explaining the gait cycle calculated when performing a gait motion.

Referring to FIG. 2 described earlier, the autonomous control unit 80 for the control device 20 in the gait disorder support apparatus 1 calculates an occurrence timing regarding the left leg, on which the power unit 2 is mounted, as the gait cycle among occurrence timings of peak values of the load imposed on the front foot parts of the foot sole surfaces detected by the FRF sensors 50 of the dedicated shoes 4A, 4B where the power unit 2 is mounted.

Subsequently, when the gait cycle fails to satisfy a predetermined threshold value continuously for a specified number of times or more, the autonomous control unit 80 detects this as an onset sign of the gait disorder associated with the wearer's motor symptom.

When the onset sign of the gait disorder is not detected as a result of this detection, it is necessary for the wearer to not be hindered by the power unit 2 from walking when swinging the wearer's legs forward during the normal gait. For this purpose, the autonomous control unit 80 controls the drive unit 10 so that the driving torque by the drive unit 10 will not hinder the wearer's gait motion.

Now, a motion assist control method by which the driving torque by the drive unit 10 will not hinder the wearer's gait motion will be explained.

During a period of time when the onset sign of the gait disorder is not detected, the autonomous control unit 80 causes output torque during the normal gait, which is the sum of viscous friction compensating torque applied to the drive unit 10 and gravity compensating torque applied to the first and second transmission members (frames) 12, 14, to act as the driving torque by the drive unit for not hindering the wearer's gait motion.

Figure 7:
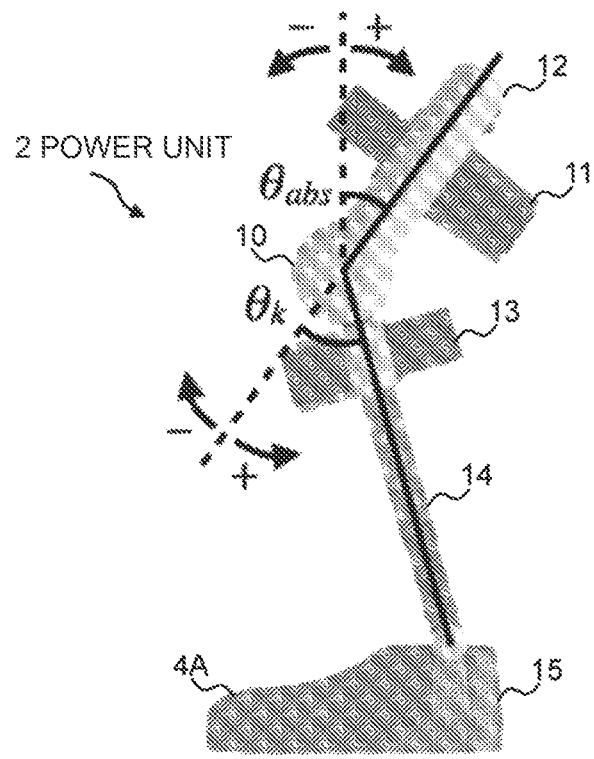
FIG. 7 is a conceptual diagram for explaining viscous friction torque and gravity compensating torque.

Referring to FIG. 7, when the knee joint angle is defined as $\theta_k$, the absolute angle relative to the vertical direction of the thigh part is defined as $\theta_{abs}$, the lower leg weight is defined as m, the lower leg length is defined as l, and viscosity of the power unit is defined as $D_{act}$, viscous friction compensating torque $\tau_{Dcomp}$, gravity compensating torque $\tau_{gcomp}$, and output torque $\tau_{LOCO}$ during the normal gait are expressed as the following Expressions (6) to (8), respectively.

[Math. 6]

$$\tau_{Dcomp} = D_{act}\dot{\theta}_k \qquad (6)$$

[Math. 7]

$$\tau_{gcomp} = \tfrac{1}{2}mgl \sin(\theta k - \theta_{abs}) \qquad (7)$$

[Math. 8]

$$\tau_{LOCO} = \tau_{Dcomp} + \tau_{gcomp} \qquad (8)$$

Accordingly, as the autonomous control unit 80 controls the output torque $\tau_{Loco}$ during the normal gait as the assist power of the drive unit 10, the wearer can walk without being hindered by the driving torque by the drive unit 10 during the normal gait.

(5) Drive Unit Control Method when Frozen Gait Onset Sign is Detected

On the other hand, when the onset sign of the gait disorder associated with the wearer's motor symptom is detected as described earlier, the autonomous control unit 80 detects the gravity center position during the wearer's gait motion from changes in the load measured by each FRF sensor 50 of the one pair of dedicated shoes 4A, 4B in order for the power unit 2 to cause the wearer's knee joint to bend.

For the purpose of securing the safety of the wearer's gait motion, the autonomous control unit 80 controls the drive unit 10 so as to cause the drive unit 10 to provide the assist power in synchronization with timing when the gravity center position is located at the wearer's leg on which the drive unit 10 is not mounted.

Now, a method for controlling the assist power generated by the drive unit 10 when the frozen gait onset sign is detected will be explained. When the frozen gait onset sign is detected, the power unit 2 performs the motion assist to bend the knee joint to a target angle as the motion assist. In this embodiment, the target angle is set as 65 degrees which is a maximum bending position during gait.

When the motion assist actually starts, a stretch reflex occurs due to a sudden joint assist motion, which induces actions of antagonist muscles against the driving torque as the motion support (hereinafter referred to as the "support torque"). Accordingly, in this embodiment, smoothing processing is executed upon start-up of generation of the support torque by the drive unit 10.

When the target angle is defined as $\theta_{target}$, assist gain is defined as $\alpha$, maximum duration of the motion assist is defined as $t_{threshold}$, and current motion assist duration is defined as $t_{assist}$, the support torque $T_{FOG}$ when the frozen gait onset sign is detected is expressed as the following Expression (9).

[Math. 9]

$$\tau_{FOG} = \begin{cases} \dfrac{1 - \cos(4\pi t_{assist})}{2} \cdot (\theta_{target} - \theta_k)\beta (0 \leq t_{assist} \leq 0.25) \\ (\theta_{target} - \theta_k)\beta (0.25 < t_{assist} < t_{threshold}) \end{cases} \quad (9)$$

Figure 8:
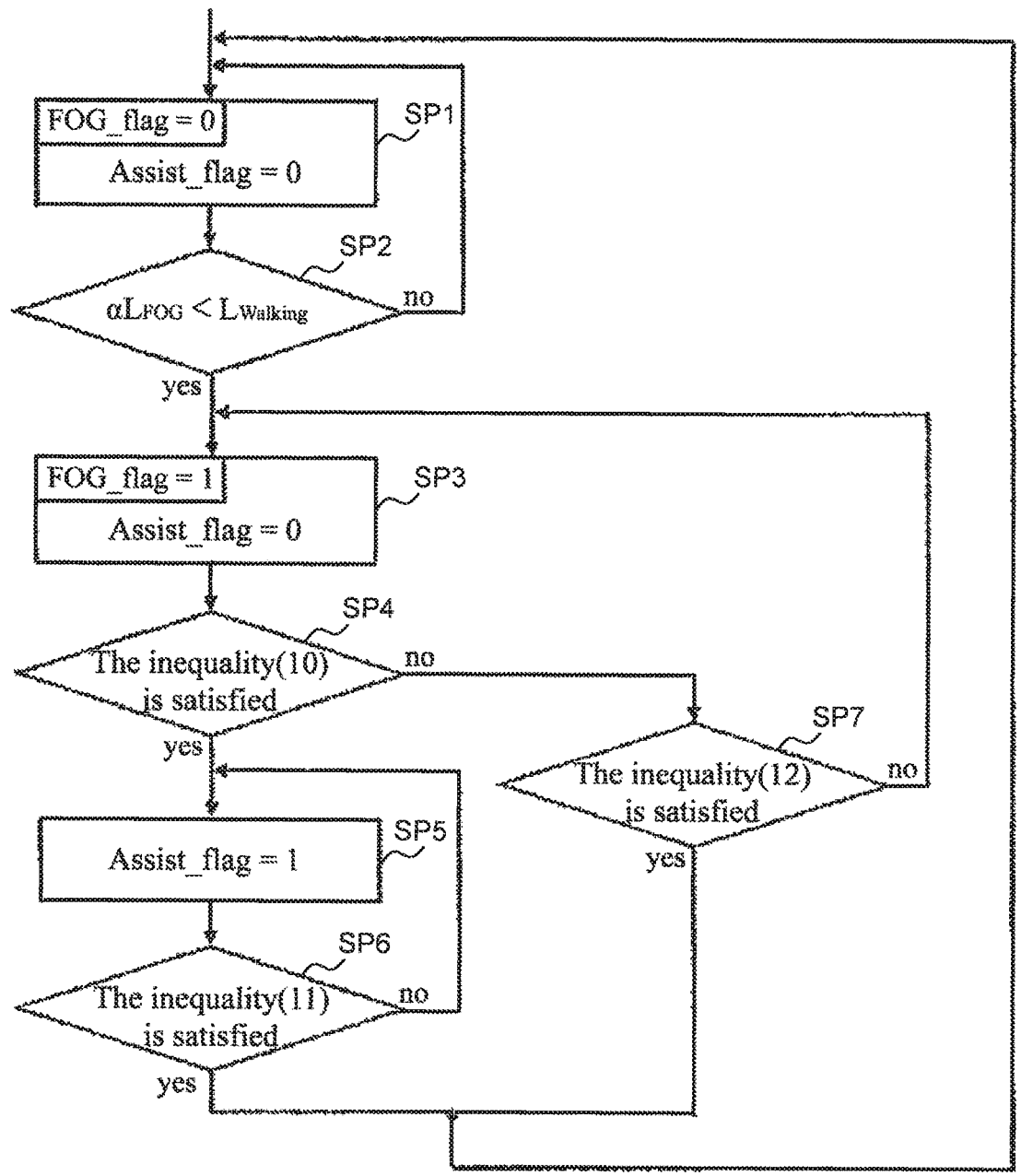
FIG. 8 is a flowchart illustrating a processing sequence for a motion assist control structure for a wearer.

FIG. 8 illustrates a processing sequence for a motion assist control structure for the wearer by the gait disorder support apparatus 1. Regarding switching of the control method between during the normal gait and upon detection of the frozen gait onset sign, the transition is made based on floor reaction force information knee joint angle information.

Under this circumstance, a frozen gait flag (FOG_flag) is set to 1 when the frozen gait is detected; an assist flag (Assist_flag) is set to 1 during the motion assist; and the respective flags are set to 0 when the relevant condition is not satisfied. The autonomous control unit 80 starts both the frozen gait flag and the assist flag from 0 when activating the control system; and while the wearer continues the normal gait motion, it maintains the frozen gait flag and the assist flag as 0 (SP1).

Subsequently, the autonomous control unit 80: calculates the gait cycle based on the FRF data on the side where the power unit 2 is mounted; judges whether or not the frozen gait onset sign is detected by the aforementioned frozen gait detection method (the frozen gait onset detection condition according to Expression (4)) (SP2); and determines that there is an onset sign of the gait disorder (frozen gait) associated with the motor symptom when it is detected.

Then, the autonomous control unit 80 performs the motion assist by setting the frozen gait flag to 1 when detecting the frozen gait onset sign, and setting the assist flag to 1 at appropriate timing to prevent the wearer from falling down based on the floor reaction force information (SP3).

When adjustment gain for judgment of a supporting leg is defined as $\gamma$, an upper limit of motion assist duration is defined as $t_{threshold}$, and a target angle when bending the knee joint is defined as $\theta_{target}$, an assist flag changing condition, a motion assist continuation condition, and a normal gait resumption condition after the detection of the frozen gait are expressed as the following Expressions (10) to (12), respectively.

[Math. 10]

$$\gamma FRF_{left} < FRF_{right} \text{ and } 1 < t \quad (10)$$

[Math. 11]

$$\theta_{target} < \theta_{knee} \text{ and } t_{threshold} < t_{assist} \quad (11)$$

[Math. 12]

$$\alpha L_{FOG} > L_{Walking} \quad (12)$$

When the knee joint of the supporting leg is bent by the motion assist, the wearer may possibly fall down due to buckling of the knee. So, when the frozen gait detection flag is 1, supporting leg judgment on the right leg where the control system is not mounted is conducted based on the FRF data from the right and left dedicated shoes 4A, 4B (SP4). When a foot pressure center position is located for one second or longer on the supporting leg side, the motion assist is performed by keeping the assist flag at 1 (SP5). Then, during the motion assist, the autonomous control unit 80 continues the motion assist by keeping the assist flag at 1 until the knee joint angle $\theta_{knee}$ exceeds the target angle $\theta_{target}$ and until the motion assist duration $t_{assist}$ exceeds the maximum duration $t_{threshold}$ (SP6).

Furthermore, the situation is assumed where the duration of the frozen gait is extremely short and the wearer resumes walking by themselves as quickly as possible. So, when the frozen gait flag is 1 and the assist flag is 0 and the normal gait resumption condition after the detection of the frozen gait is satisfied and the wearer's gait condition is thereby judged as the normal gait by the frozen gait detection method, the frozen gait flag is set to 0 (SP7).

Accordingly, as the autonomous control unit 80 controls the support torque $T_{FOG}$ upon detection of the frozen gait onset sign as the assist power of the drive unit 10, the wearer can perform the gait motion by repeating the motion to bend their knee joint to the target angle upon the onset sign of the gait disorder and then the motion to extend their knee joint.

Furthermore, by executing the smoothing processing at the start-up of generation of the support torque of the drive unit 10, it is possible to prevent the induction of the antagonist muscles against the support torque $T_{FOG}$ and avoid the occurrence of physical burdens at the moment when the support torque $T_{FOG}$ is applied to the wearer and the joint assist motion is started.

Figure 9:
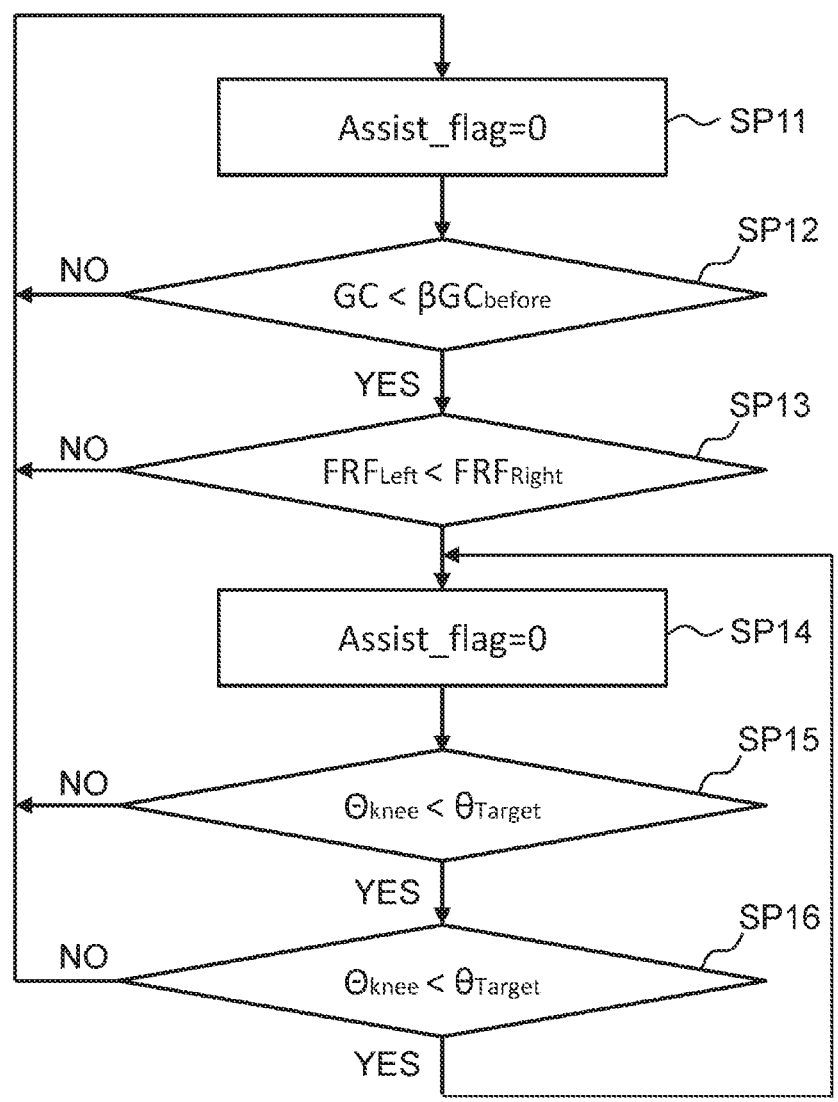
FIG. 9 is a flowchart illustrating a processing sequence for a complementary motion assist control structure for the wearer.

In this embodiment, the gait disorder support apparatus 1 may not only execute the processing sequence for the motion assist control structure for the wearer as described above, but also complementarily execute a motion assist control structure as illustrated in FIG. 9. Referring to FIG. 9, the autonomous control unit 80: starts the assist flag from 0 when activating the control system; and continues the assist flag as 0 while the wearer continues the normal gait motion (SP11).

Subsequently, the autonomous control unit 80 calculates the gait cycle based on the FRF data on the side where the power unit 2 is mounted and judges whether or not it has detected a reduction in the gait cycle continuously for a specified number of times or more (SP12); and when the above-described reduction in the gait cycle is detected, the autonomous control unit 80 determines that there is an onset sign of the gait disorder (frozen gait) associated with the motor symptom.

Then, the autonomous control unit 80 judges: the gravity center position based on the FRF data from the right and left dedicated shoes 4A, 4B (SP13); and performs the motion assist by setting the assist flag to 1 when such judgment is made (SP14).

During the motion assist, the autonomous control unit 80 continues the motion assist by setting the assist flag to 1 until the knee joint angle $\theta_{knee}$ exceeds the target angle $\theta_{target}$ (SP15) or until the motion assist duration $t_{assist}$ exceeds the maximum duration $t_{threshold}$ (SP16).

Accordingly, the autonomous control unit 80 controls the support torque $T_{FOG}$ upon the detection of the frozen gait onset sign as the assist power of the drive unit 10 in the same manner as described earlier by complementing the detection of the frozen gait onset sign. This control of the autonomous control unit 80 enables the wearer to perform the gait motion by repeating the motion to bend the knee joint to the target angle upon the onset sign of the gait disorder and then the motion to extend the knee joint.

Furthermore, this embodiment has described the case where the power unit 2 performs the motion assist of the wearer's knee joint to the target angle (65 degrees) which is the maximum bending position during gait; however, the present invention is not limited to this example and the generation timing and duration of the assist power to be generated by the drive unit 10 may be adjusted in accordance with the wearer's gait motion condition.

For example, when the degree of onset of the wearer's gait disorder is relatively light, the support torque $T_{FOG}$ by the drive unit 10 may be applied to the degree of slightly prompting the wearer's own gait motion. Basically, as long as the state where any frozen gait onset sign is no longer detected can be maintained while always monitoring the gait cycle and the gravity center position, the degree of application of the support torque $T_{FOG}$ may be freely adjusted in accordance with the wearer's gait motion condition.

(6) Experiment Results

Figure 10:
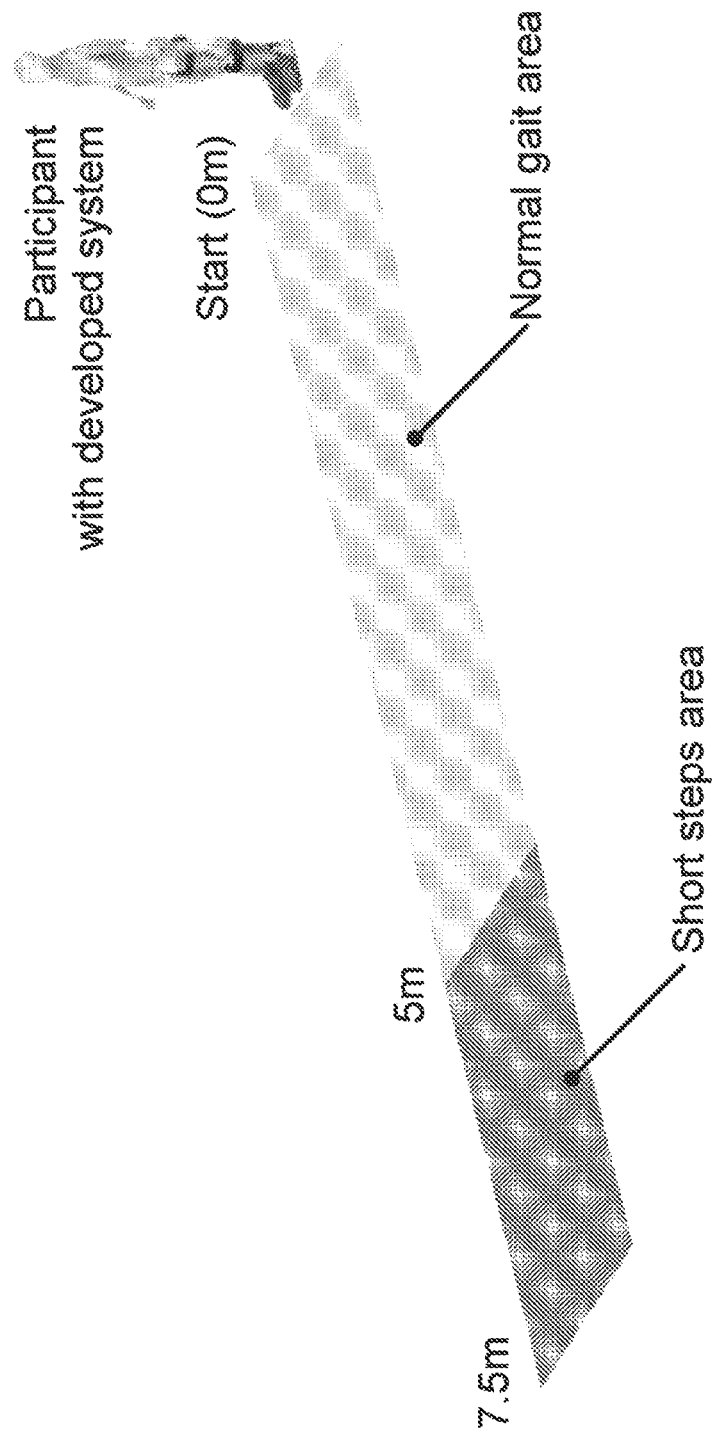
FIG. 10 is a conceptual diagram illustrating an experiment environment in a state where the gait disorder support apparatus is mounted.

Experiments were actually conducted as illustrated in FIG. 10 in a state where the wearer wore the gait disorder support apparatus 1 according to this embodiment. There was one wearer who was a healthy male of 24 years old with the height of 165 cm and the body weight of 62 kg. This wearer performed the normal gait in a section from 0 m to 5 m and then performs a frozen gait simulating motion in a section from 5 m to 7.5 m. This sequence of motions was considered as one operation, which was carried out 10 times. When this experiment was conducted, the frozen gait simulating motion was performed by walking in small motions with short steps.

Figure 11:
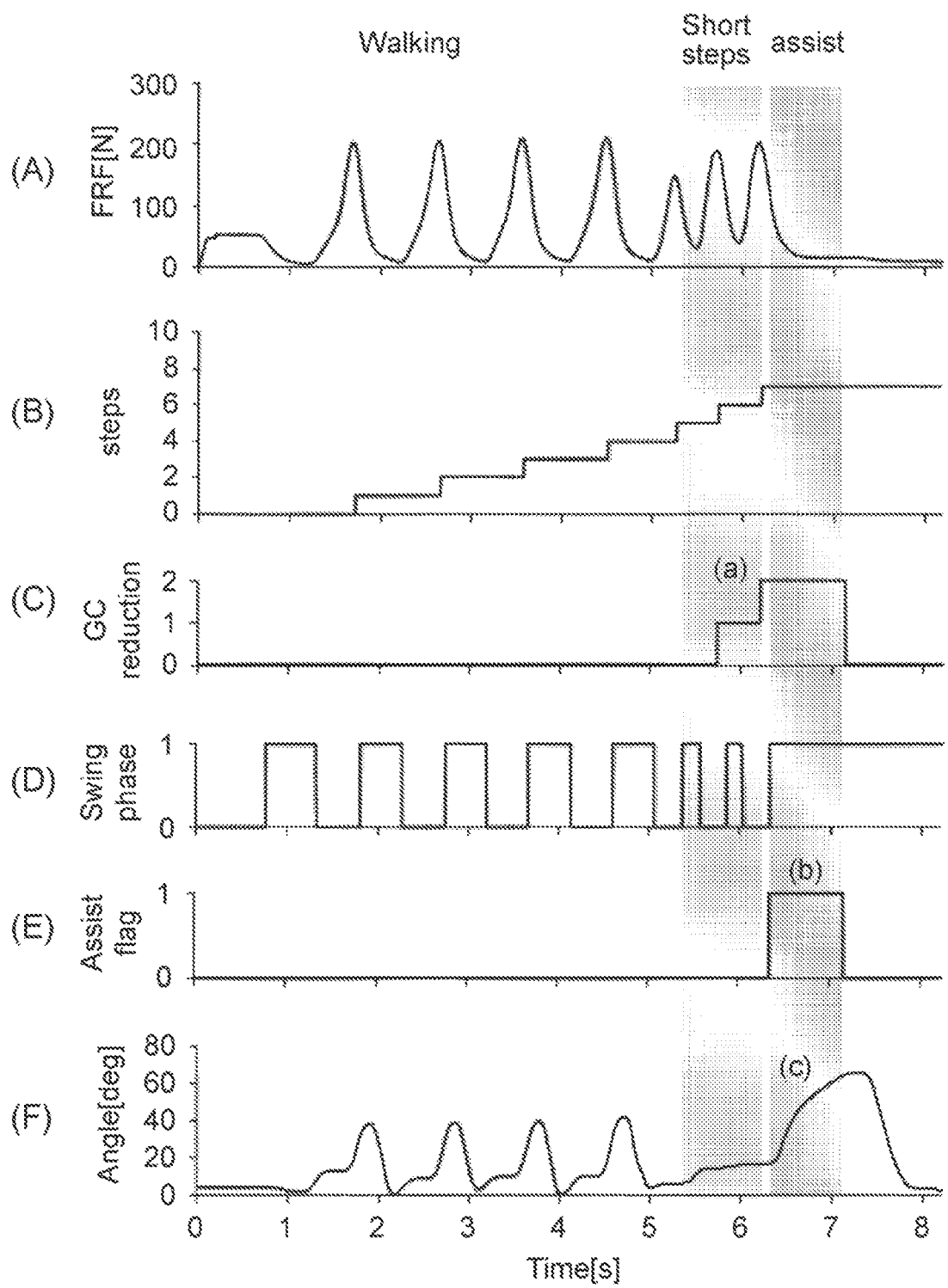
FIG. 11 is a timing chart illustrating a motion assist state when the wearer is performing a gait motion.

FIG. 11 illustrates an example of the experiment results. It was confirmed that regarding the FRF data which represents the load on the foot soles, when the transition was made from the normal gait "Walking" to the frozen gait simulating motion "Short steps" (FIG. 11A and FIG. 11B), a reduction in the gait cycle was continuously detected ((a) in FIG. 11C and FIG. 11D); and the motion assist was performed by changing the assist flag from 0 to 1 on the basis of the gravity center position ((b) in FIG. 11E) and the knee joint was bent to the target angle of 65 degrees ((c) in FIG. 11F).

(7) Experiment Results by Other Methods

Figure 12:
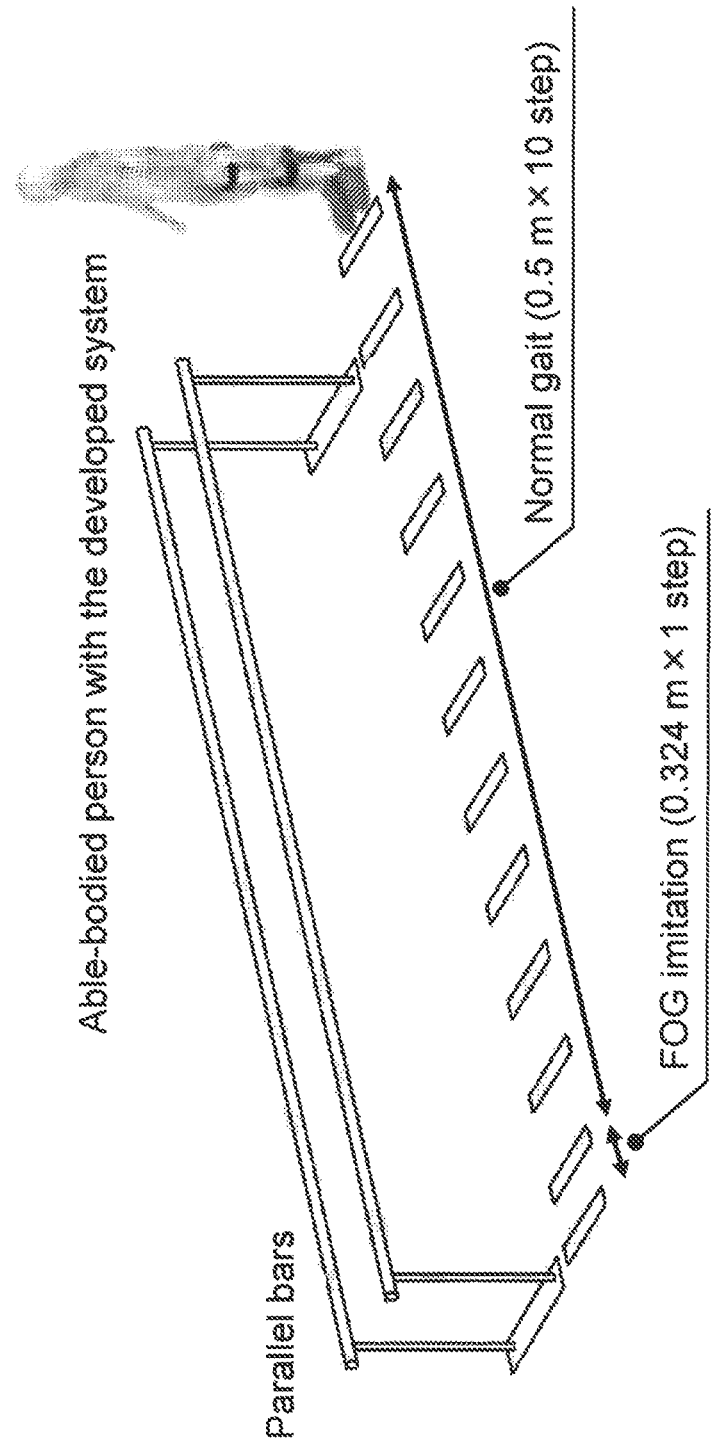
FIG. 12 is a conceptual diagram illustrating an experiment environment of another embodiment in a state where the gait disorder support apparatus is mounted.

Besides the above-mentioned experiment, an experiment as illustrated in FIG. 12 was conducted in a state where the wearer wore the gait disorder support apparatus 1 according to this embodiment. This wearer performed the normal gait for the section from 0 m to 5 m and then performed the frozen gait simulating motion by walking in small motions with one smaller steps.

Under this circumstance, in consideration of the fact that the gait cycle upon the onset of the frozen gait reduces by 35.2% as compared to the immediately preceding normal gait, lines were drawn on the floor face so that the step lengths of the normal gait and the frozen gait simulating motion would become 0.5 m and 0.348 m, respectively; and the wearer walked by using the lines as indications. Providing these lines which serve as the indications ensures objectivity and reproducibility of the motion simulating the Parkinson's disease patient upon the onset of the frozen gait. Regarding this experiment, an operation was performed 5 times as calibration and then the operation was performed 10 times after the calibration.

Figure 13:
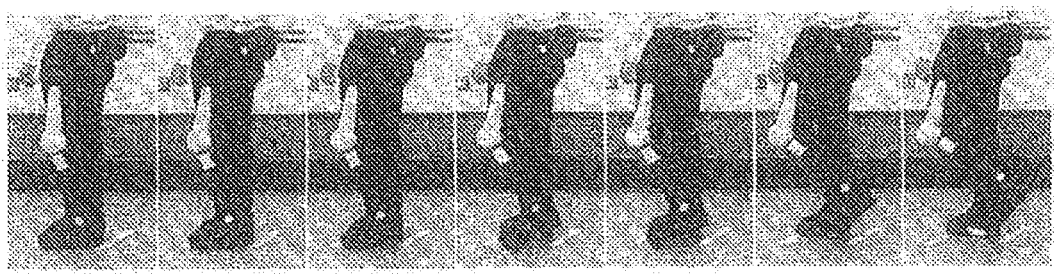
FIG. 13 is a continuity chart illustrating how the motion assist is performed during a frozen gait simulating motion.
Figure 14:
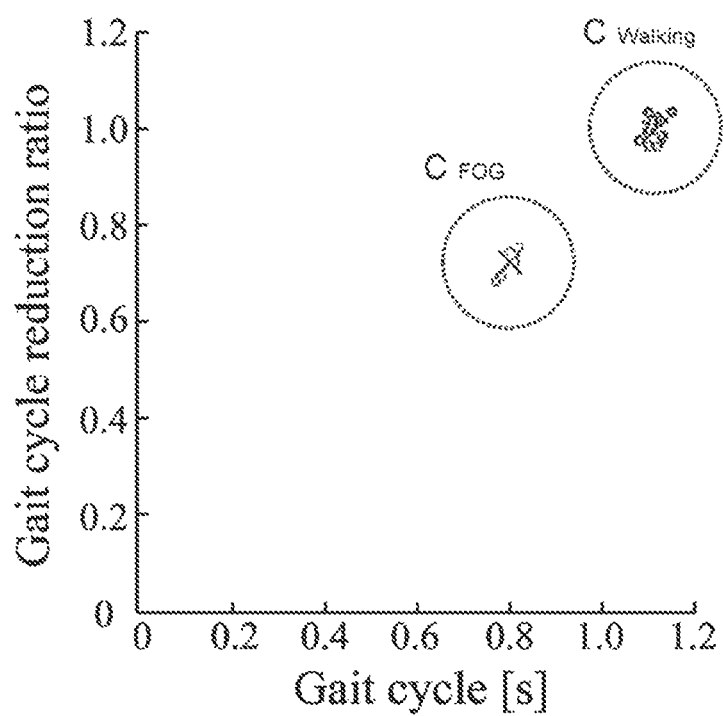
FIG. 14 is a chart illustrating the correlation between a gait cycle and its reduction ratio.

FIG. 13 illustrates how the motion assist is performed during the frozen gait simulating motion; and FIG. 14 illustrates the results of cluster analysis of measured data at the time the calibration. In FIG. 14, ○ represents each data at the time of the calibration and x represents the centroid. Also, in FIG. 14, $C_{Walking}$ represents during the normal gait and $C_{FOG}$ represents during the frozen gait simulating motion.

Figure 15:
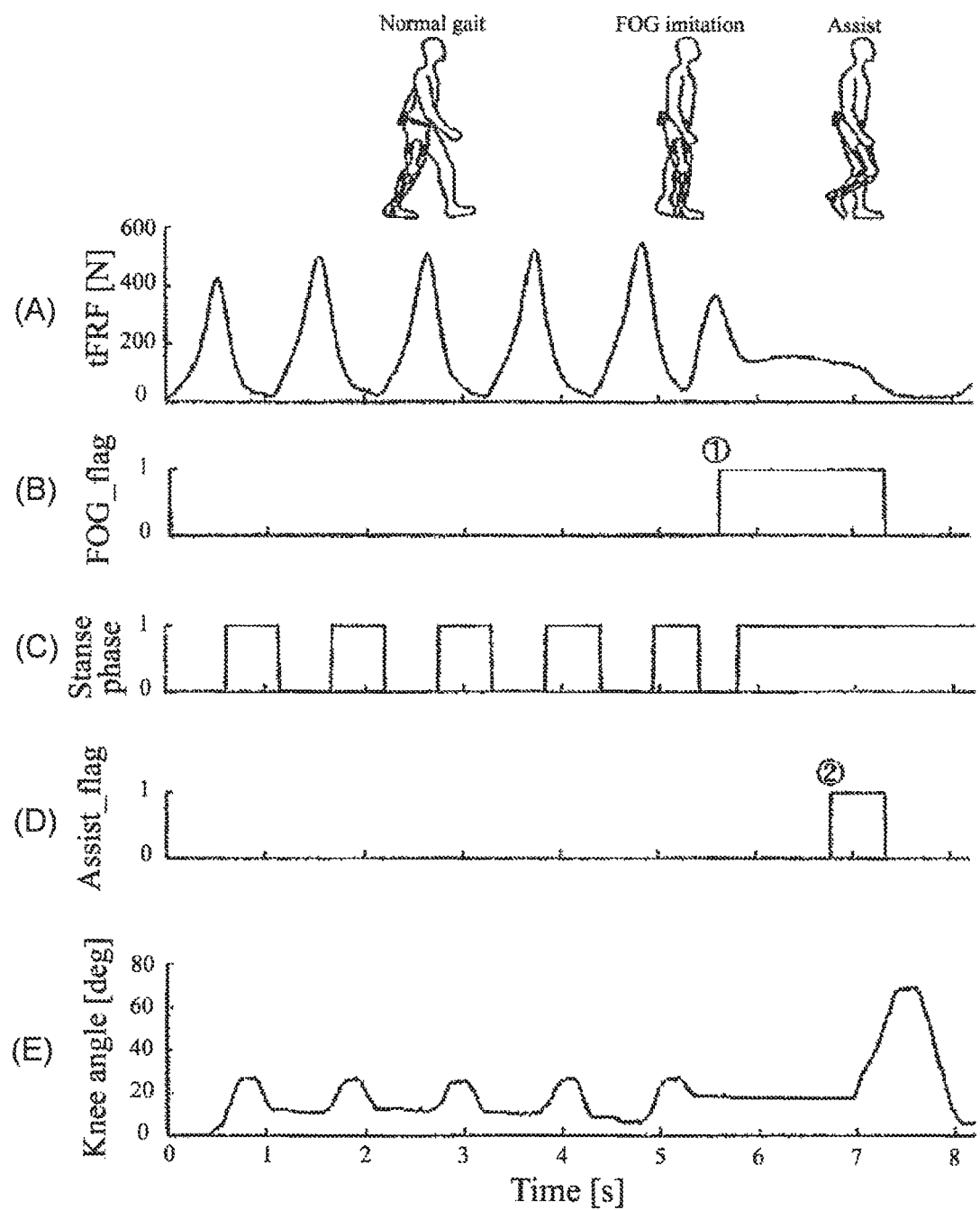
FIG. 15 is a timing chart illustrating the motion assist state when the wearer is performing the gait motion.

Furthermore, FIG. 15 illustrates the results of trial tests after setting a threshold by the calibration. FIG. 15A illustrates how the transition of the left-foot toe floor reaction force tFRF was made along with the passage of time. Also, FIG. 15B illustrates how the transition of the FOG_flag representing detection of the onset of the frozen gait was made along with the passage of time. Moreover, FIG. 15C illustrates how the transition of "Stance phase" for judging the stance phase on the side where the control system was not mounted was made along with the passage of time. Furthermore, FIG. 15D illustrates how the transition of the Assist_flag representing the flag to perform the motion assist was made along with the passage of time. Furthermore, FIG. 15E illustrates how the transition of the knee joint angle "Knee angle" was made along with the passage of time.

The centroids of the clusters during the normal gait and during the frozen gait simulating motion are (1.12, 1.19) and (0.81, 0.72), respectively (FIG. 14); and the measured data were properly classified in all respects. Regarding the trials conducted 10 times after the calibration, it was confirmed that the motion assist was performed to bend the wearer's knee joint in all the trials. It should be noted that the motion assist is executed as the frozen gait detection flag is turned to 1 as indicated with (1) in FIG. 15B and then the motion assist flag is turned to 1 as indicated with (2) in FIG. 15D. Incidentally, the frozen gait detection flag is judged based on the result of the cluster analysis during the frozen gait simulating motion. Furthermore, the motion assist flag is judged based on the supporting leg judgment on the side where the system is not mounted.

Furthermore, it was also confirmed that the motion assist was not performed during the normal gait, when active walking was stopped, and when the side where the control system was mounted was the supporting leg.

Figure 16:
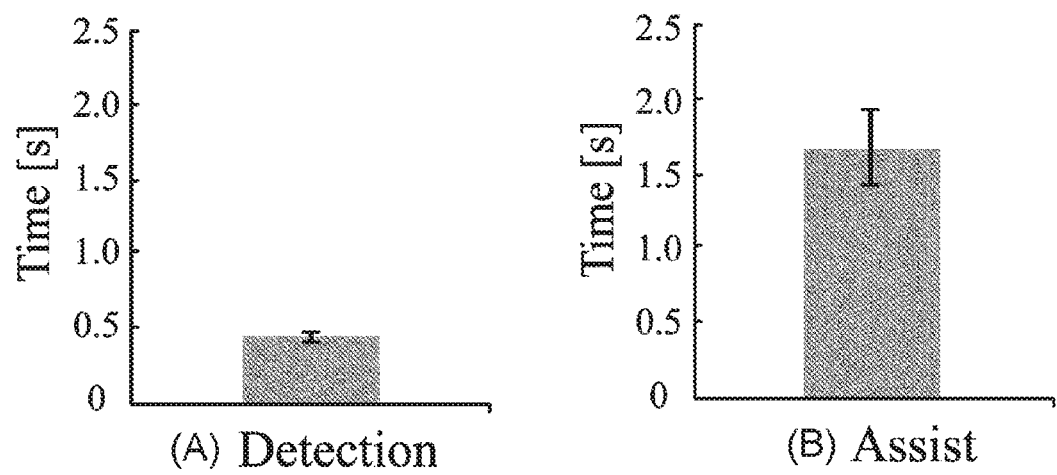
FIG. 16 is a diagram for explaining a lag in detection after calibration.

FIG. 16A illustrates a response lag in the detection of the frozen gait simulating motion after the calibration and FIG. 16B illustrates a response lag in the motion assist. An error bar in each drawing represents a standard deviation. Average time of the response lag in the detection was 0.42 seconds and average time of the response lag of the motion assist was 1.67 seconds.

(8) Other Embodiments

This embodiment has described the case where the gait disorder support apparatus 1 is of the single leg structure to mount the power unit 2 around the knee joint of the wearer's left leg; however, the present invention is not limited to this example and the gait disorder support apparatus 1 may be of a single leg structure for the right leg or may further be of a two-leg structure for both the left leg and the right leg basically as long as the motion assist can be performed so that the leg(s) can be moved to step forward with the motion support from outside.

Furthermore, this embodiment has described the case where the frozen gait is applied as the gait disorder associated with the motor symptom; however, the present invention is not limited to this example and the motor symptom includes tremor, rigidity, akinesia, hypokinesis, muscle rigidity, postural reflex disorder, and so on, so that the present invention can be applied to wide variety of disorders, other than the frozen gait, which may influence the lower half of the body in association with various motor symptoms.

Furthermore, this embodiment has described the case where the FRF sensor 50 (the foot load measurement unit) mounted on the one pair of dedicated shoes 4A, 4B is designed so that the foot sole surface is divided into the front foot part and the rear foot part and the FRF sensor 50 can measure the load on these parts independently; however, the present invention is not limited to this example and the position to locate the FRF sensor can be freely set as long as the load on the front foot parts (toe parts) of the foot sole surfaces is measured in order to detect the gait cycle and the load at each site of the foot sole in contact with the ground can be measured along with movements of the center of gravity at the rear foot part (heel part), an outer arch (from the heel part to the root of a little toe), an inner arch (from the heel part to the root of a big toe), and the big toe part in order to detect the gravity center position.

Furthermore, this embodiment has described the case where the control device 20 (mainly the autonomous control unit 80) and the data storage unit 21 in the power unit 2 execute the gait cycle calculation unit which calculates the gait cycle, the onset sign detection unit which detects the onset sign of the gait disorder associated with the wearer's motor symptom, and the control unit which controls the drive unit 10 depending on whether the onset sign is detected or not; however, the present invention is not limited to this example and the gait cycle calculation unit, the onset sign detection unit, and the control unit may be executed by using a single control means.

Furthermore, this embodiment has described the case where the parameters regarding the motions of the control system are input from the potentiometer 30, the absolute angle sensor 31, and the biological signal detection unit 32; however, the present invention is not limited to this example and the parameters regarding the motions of the control system may be set by using a dedicated controller (which is not illustrated in the drawings). The wearer's walking information is displayed on a display screen of this dedicated controller. This walking information includes the gait cycle, input samples during gait, Euclidean distances between the centroids of the respective clusters, and foot pressure center positions. Moreover, adjustable parameters are adjustment gain of an assist amount of the control system and detection sensitivity for the frozen gait detection method (the frozen gait onset condition according to Expression (4) mentioned earlier).

Figure 17:
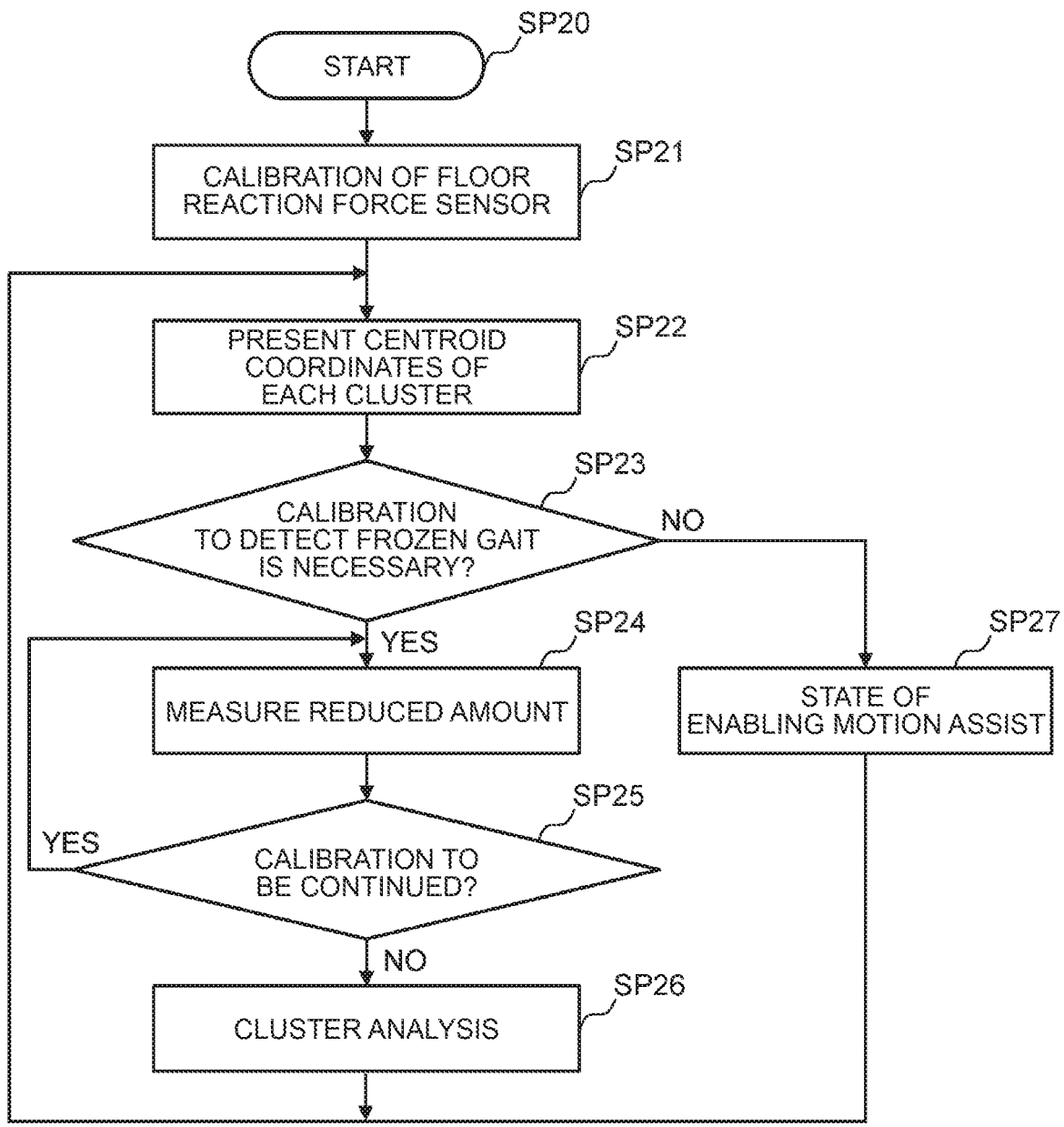
FIG. 17 is a flowchart illustrating an operation processing sequence using a dedicated controller.

FIG. 17 illustrates a flow of motions by the dedicated controller. When the control system is activated (SP20), the calibration of the FRF sensors 50 is firstly performed (SP21). Then, the centroid coordinates of the respective clusters used for the frozen gait detection method in the immediately preceding operation are presented (SP22) and whether the calibration should be executed on the centroid coordinates or not is selected (SP23).

When the wearer uses this control system for the first time or the calibration is necessary due to a change in the disease state, the execution of the calibration is selected on the controller and a reduced amount of the immediately preceding gait cycle as compared to the gait cycle of the normal gait is measured (SP24). Incidentally, upon the execution of this calibration, measurement of an upright standing position, measurement of the gait cycle of the normal gait, and measurement of the gait cycle in the frozen gait motion may be performed other than the measurement of the reduced amount.

Subsequently, by selecting the termination of the calibration (SP25), the cluster analysis within the control system is conducted (SP26), the respective centroid coordinates are presented in the same manner as at the time of the activation of the control system (SP22) and subsequent processing is executed. If the calibration is necessary again, the execution is selected; and if the calibration is not necessary, the coordinates calculated by the cluster analysis are set so as to enter the state of enabling the motion assist (SP27).

REFERENCE SIGNS LIST

1: gait disorder support apparatus
2: power unit
3: lower back belt
4A, 4B: dedicated shoes
10: drive unit
11, 13: fastening members
12: first transmission member
14: second transmission member
15: held part
16: battery unit
20: control device
21: data storage unit
23: reference parameter database
30: potentiometer
31: absolute angle sensor
32: biological signal detection unit
40: voluntary control unit
50: FRF sensor
51: FRF control unit
52: transmitter
60: receiver
70: phase specifying unit
80: autonomous control unit

The invention claimed is:
1. A gait disorder support apparatus assisting one leg of a wearer comprising:
   a power unit configured to be mounted around a knee joint of only one of either a right leg or a left leg of the wearer, such that gait disorder support apparatus does not assist an other of the left leg or the right leg of the wearer;
   a lower back unit configured to be mounted at a lower back of the wearer; and
   a pair of shoes configured to be worn by both feet of the wearer, wherein the power unit includes an actuator and a drive unit that is configured to drive frames configured to be mounted on a thigh part and a lower leg part relatively around a rotation axis corresponding to the knee joint of the wearer, wherein each of the pair of shoes is configured to hold a wearer's foot from toes to an angle, includes a floor reaction force sensor at a shoe sole, and is capable of measuring a load by using the sensor, wherein the power unit includes:

a gait cycle calculation unit calculates, as a gait cycle of a wearer, an occurrence timing regarding the leg on which the drive unit is mounted among occurrence timings of a peak value of the measured load;

an onset sign detection unit detects a sign indicating a possible onset of a gait disorder associated with a motor symptom of the wearer on a basis of a correlation between the gait cycle calculated by the gait cycle calculation unit and a reduction ratio of the gait cycle as compared to a gait cycle calculated immediately before the above-mentioned calculation; and a control unit that controls the drive unit so that the drive unit applies assist power to the knee joint of the wearer when the sign indicating the possible onset of the gait disorder is detected by the onset sign detection unit, while controlling the drive unit so that driving torque by the drive unit does not interfere with a gait motion of the wearer when the sign indicating the possible onset of the gait disorder is not detected, and wherein the control unit generates the assist power in synchronization with timing when a gravity center position of the wearer is located at the wearer's leg on which the drive unit is not mounted.

2. The gait disorder support apparatus according to claim 1, wherein, when the gait cycle calculated by the gait cycle calculation unit fails to satisfy a predetermined threshold value continuously for a specified number of times or more, the onset sign detection unit is configured to detect the gait cycle as the sign indicating the possible onset of the gait disorder associated with the motor symptom of the wearer.

3. The gait disorder support apparatus according to claim 1, wherein the floor reaction force sensor is configured to measure the load imposed not only on a front foot part of right and left foot sole surfaces of the wearer, but also on a middle foot part and a rear foot part, and wherein while detecting a gravity center position during the wearer's gait motion based on a change in the load measured by the floor reaction force sensor, the control unit is configured to control the drive unit so that the drive unit applies the assist power in synchronization with timing when the gravity center position is located at the wearer's leg on which the drive unit is not mounted.

4. The gait disorder support apparatus according to claim 1, wherein, when the sign indicating the possible onset of the gait disorder is detected by the onset sign detection unit, the control unit is configured to adjust size and duration of the assist power generated by the drive unit in accordance with a gait motion condition of the wearer.

5. The gait disorder support apparatus according to claim 4, wherein the control unit is configured to execute specified smoothing processing for a specified amount of time after generation of the driving torque is started by the drive unit.

6. The gait disorder support apparatus according to claim 1, wherein during a period of time when the sign indicating the possible onset of the gait disorder is not detected by the onset sign detection unit, the control unit is configured to cause a sum of viscous friction compensating torque applied to the drive unit and of a gravity compensating torque applied to the frames to act as the driving torque by the drive unit in order to not hinder the gait motion of the wearer.

7. A gait disorder support method for controlling a gait disorder support apparatus having a drive unit configured for driving frames mounted on a thigh part and a lower leg part of only one of either a right leg or a left leg of a wearer relatively around a rotation axis corresponding to a knee joint of the wearer such that the gait disorder support apparatus does not assist an other of the left leg or the right leg of the wearer, wherein the gait disorder support method comprises:

first processing for measuring a load imposed on a front foot part of each of right and left foot sole surfaces of the wearer and calculating, as a gait cycle, an occurrence timing regarding the leg on which the drive unit is mounted among occurrence timings of a peak value of the measured load;

second processing for detecting a sign indicating a possible onset of a gait disorder associated with a motor symptom of the wearer on a basis of a correlation between the gait cycle and a reduction ratio of the gait cycle as compared to immediately preceding gait; and third processing for controlling the drive unit for the drive unit to apply assist power to the knee joint of the wearer when the onset sign of the gait disorder is detected, while controlling the drive unit so that driving torque by the drive unit does not interfere with a gait motion of the wearer when the sign indicating the possible onset of the gait disorder is not detected, and wherein the assist power is generated in synchronization with timing when a gravity center position of the wearer is located at the wearer's leg on which the drive unit is not mounted.

8. The gait disorder support method according to claim 7, wherein in the second processing, when the gait cycle fails to satisfy a predetermined threshold value continuously for a specified number of times or more, the gait cycle is detected as the sign indicating the possible onset of the gait disorder associated with the motor symptom of the wearer.

9. The gait disorder support method according to claim 7, wherein in the first processing, the load imposed not only on the front foot part of the right and left foot sole surfaces of the wearer, but also on a middle foot part and a rear foot part is measured, and wherein in the third processing, while a gravity center position during the wearer's gait motion is detected based on a change in the measured load, the drive unit is controlled so that the drive unit applies the assist power in synchronization with timing when the gravity center position is located at the wearer's leg on which the drive unit is not mounted.

10. The gait disorder support method according to claim 7, wherein in the third processing, when the sign indicating the possible onset of the gait disorder is detected by the second processing, size and duration of the assist power generated by the drive unit are adjusted in accordance with a gait motion condition of the wearer.

11. The gait disorder support method according to claim 10, wherein in the third processing, specified smoothing processing is executed for a specified amount of time after generation of the driving torque is started by the drive unit.

12. The gait disorder support method according to claim 7, wherein in the third processing during a period of time when the onset sign is not detected by the second processing, a sum of viscous friction compensating torque applied to the drive unit and gravity compensating torque applied to the frames are caused to act as the driving torque by the drive unit in order to not hinder the gait motion of the wearer.

\* \* \* \* \*